United States Patent
Altarac et al.

(10) Patent No.: US 9,861,398 B2
(45) Date of Patent: Jan. 9, 2018

(54) INTERSPINOUS SPACER

(71) Applicant: VertiFlex, Inc., San Clemente, CA (US)

(72) Inventors: Moti Altarac, Irvine, CA (US); Shawn Tebbe, Oceanside, CA (US); Joey Camia Reglos, Lake Forest, CA (US); Yang Cheng, Foothill Ranch, CA (US)

(73) Assignee: VertiFlex, Inc., Carlsbad, CA (US)

( * ) Notice: Subject to any disclaimer, the term of this patent is extended or adjusted under 35 U.S.C. 154(b) by 25 days.

(21) Appl. No.: 14/835,195

(22) Filed: Aug. 25, 2015

(65) Prior Publication Data
US 2016/0045232 A1    Feb. 18, 2016

Related U.S. Application Data

(60) Division of application No. 13/406,442, filed on Feb. 27, 2012, now Pat. No. 9,119,680, which is a
(Continued)

(51) Int. Cl.
*A61B 17/70*    (2006.01)
*A61B 17/56*    (2006.01)

(52) U.S. Cl.
CPC ...... *A61B 17/7067* (2013.01); *A61B 17/7065* (2013.01); *A61B 2017/564* (2013.01)

(58) Field of Classification Search
CPC ...... A61B 17/7062–17/7068; A61B 2017/564; A61B 17/70; A61B 17/7065; A61B 17/7067
See application file for complete search history.

(56) References Cited

U.S. PATENT DOCUMENTS 2,248,054 A    7/1941   Becker
2,677,369 A    5/1954   Knowles
(Continued)

FOREIGN PATENT DOCUMENTS

CA    268461 A    2/1927
CN    2794456 Y   7/2006
(Continued)

OTHER PUBLICATIONS

European Search Report Application No. EP05849654.8; Applicant: The Board of Trustees of the Leland Stanford Junior University; Date of Completion: Jun. 21, 2011, 4 pages.
(Continued)

*Primary Examiner* — Christopher D Prone
(74) *Attorney, Agent, or Firm* — Perkins Coie LLP

(57) ABSTRACT

An implantable spacer for placement between adjacent spinous processes is provided. The spacer includes a body and a wing rotatably connected to the body. The wing includes two U-shaped configurations that together define a substantially H-shaped configuration for retaining the spacer between adjacent spinous processes. An actuator assembly is connected to the body and to the wing with the proximal end of the spacer being connectable to a removable driver that is configured to engage the actuator assembly. While connected to the spacer, the driver is rotatable in one direction to deploy the wing from an undeployed to a deployed configuration and in an opposite direction to undeploy the wing. In the deployed configuration, the spacer acts as a space holder opening up the area of the spinal canal, maintaining foraminal height, reducing stress on the facet joints and relieving pain for the patient.

22 Claims, 10 Drawing Sheets

Related U.S. Application Data continuation of application No. 12/205,511, filed on Sep. 5, 2008, now Pat. No. 8,123,782, which is a continuation-in-part of application No. 12/220,427, filed on Jul. 24, 2008, now Pat. No. 8,277,488, said application No. 12/205,511 is a continuation-in-part of application No. 12/217,662, filed on Jul. 8, 2008, now Pat. No. 8,273,108, which is a continuation-in-part of application No. 12/148,104, filed on Apr. 16, 2008, now Pat. No. 8,292,922, said application No. 12/205,511 is a continuation-in-part of application No. 11/593,995, filed on Nov. 7, 2006, now Pat. No. 8,425,559, which is a continuation-in-part of application No. 11/582,874, filed on Oct. 18, 2006, now Pat. No. 8,128,662, which is a continuation-in-part of application No. 11/314,712, filed on Dec. 20, 2005, now Pat. No. 8,152,837, which is a continuation-in-part of application No. 11/190,496, filed on Jul. 26, 2005, now Pat. No. 8,409,282, which is a continuation-in-part of application No. 11/079,006, filed on Mar. 10, 2005, now Pat. No. 8,012,207, which is a continuation-in-part of application No. 11/052,002, filed on Feb. 4, 2005, now Pat. No. 8,317,864, which is a continuation-in-part of application No. 11/006,502, filed on Dec. 6, 2004, now Pat. No. 8,123,807, which is a continuation-in-part of application No. 10/970,843, filed on Oct. 20, 2004, now Pat. No. 8,167,944.

(60) Provisional application No. 60/967,805, filed on Sep. 7, 2007, provisional application No. 60/961,741, filed on Jul. 24, 2007, provisional application No. 60/958,876, filed on Jul. 9, 2007, provisional application No. 60/923,971, filed on Apr. 17, 2007, provisional application No. 60/923,841, filed on Apr. 16, 2007.

(56) References Cited

U.S. PATENT DOCUMENTS

| | | |
|---|---|---|
| 3,242,120 A | 3/1966 | Steuber |
| 3,486,505 A | 12/1969 | Morrison |
| 3,648,691 A | 3/1972 | Lumb et al. |
| 3,986,383 A | 10/1976 | Petteys |
| 4,545,374 A | 10/1985 | Jacobson |
| 4,632,101 A | 12/1986 | Freedland |
| 4,685,447 A | 8/1987 | Iversen et al. |
| 4,799,484 A | 1/1989 | Smith et al. |
| 4,863,476 A | 9/1989 | Shepperd |
| 4,895,564 A | 1/1990 | Farrell |
| 4,986,831 A | 1/1991 | King et al. |
| 5,011,484 A | 4/1991 | Breard |
| 5,015,247 A | 5/1991 | Michelson |
| 5,019,081 A | 5/1991 | Watanabe |
| 5,040,542 A | 8/1991 | Gray |
| 5,059,193 A | 10/1991 | Kuslich |
| 5,092,866 A | 3/1992 | Breard et al. |
| 5,178,628 A | 1/1993 | Otsuka et al. |
| 5,180,393 A | 1/1993 | Commarmond et al. |
| 5,182,281 A | 1/1993 | Frigola-Constansa et al. |
| 5,188,281 A | 2/1993 | Fujiwara et al. |
| 5,192,281 A | 3/1993 | de la Caffiniere |
| 5,195,526 A | 3/1993 | Michelson |
| 5,298,253 A | 3/1994 | LeFiles et al. |
| 5,368,594 A | 11/1994 | Martin et al. |
| 5,390,683 A | 2/1995 | Pisharodi |
| 5,415,661 A | 5/1995 | Holmes |
| 5,456,722 A | 10/1995 | McLeod et al. |
| 5,462,738 A | 10/1995 | LeFiles et al. |
| 5,472,452 A | 12/1995 | Trott |
| 5,484,437 A | 1/1996 | Michelson |
| 5,487,739 A | 1/1996 | Aebischer et al. |
| 5,489,308 A | 2/1996 | Kuslich et al. |
| 5,496,318 A | 3/1996 | Howland et al. |
| 5,531,748 A | 7/1996 | de la Caffiniere et al. |
| 5,549,679 A | 8/1996 | Kuslich |
| 5,571,189 A | 11/1996 | Kuslich |
| 5,591,165 A | 1/1997 | Jackson |
| 5,609,634 A | 3/1997 | Voydeville et al. |
| 5,609,636 A | 3/1997 | Kohrs et al. |
| 5,645,599 A | 7/1997 | Samani et al. |
| 5,654,599 A | 8/1997 | Casper |
| 5,658,337 A | 8/1997 | Kohrs et al. |
| 5,674,295 A | 10/1997 | Ray et al. |
| 5,700,264 A | 12/1997 | Zucherman et al. |
| 5,725,582 A | 3/1998 | Bevan et al. |
| 5,741,253 A | 4/1998 | Michelson |
| 5,746,720 A | 5/1998 | Stouder, Jr. |
| 5,762,629 A | 6/1998 | Kambin |
| 5,836,948 A | 11/1998 | Zucherman et al. |
| 5,860,977 A | 1/1999 | Zucherman et al. |
| 5,863,948 A | 1/1999 | Epstein et al. |
| 5,876,404 A | 3/1999 | Zucherman et al. |
| RE36,211 E | 5/1999 | Nonomura et al. |
| 5,904,636 A | 5/1999 | Chen |
| 5,904,686 A | 5/1999 | Zucherman et al. |
| 5,928,207 A | 7/1999 | Pisano et al. |
| 5,948,017 A | 9/1999 | Taheri |
| 5,972,015 A | 10/1999 | Scribner et al. |
| 6,039,761 A | 3/2000 | Li et al. |
| 6,045,552 A | 4/2000 | Zucherman et al. |
| 6,048,342 A | 4/2000 | Zucherman et al. |
| 6,048,345 A | 4/2000 | Berke et al. |
| 6,066,154 A | 5/2000 | Reiley et al. |
| 6,068,630 A | 5/2000 | Zucherman et al. |
| 6,074,390 A | 6/2000 | Zucherman et al. |
| 6,080,155 A | 6/2000 | Michelson |
| 6,080,157 A | 6/2000 | Cathro et al. |
| 6,090,112 A | 7/2000 | Zucherman et al. |
| 6,096,038 A | 8/2000 | Michelson |
| 6,102,928 A | 8/2000 | Bonutti |
| D433,193 S | 10/2000 | Gaw et al. |
| 6,132,464 A | 10/2000 | Martin |
| 6,149,642 A | 11/2000 | Gerhart et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,215 A | 12/2000 | Urbahns et al. |
| 6,179,873 B1 | 1/2001 | Zientek |
| 6,183,471 B1 | 2/2001 | Zucherman et al. |
| 6,190,387 B1 | 2/2001 | Zucherman et al. |
| 6,225,048 B1 | 5/2001 | Soderberg-Naucler et al. |
| 6,235,030 B1 | 5/2001 | Zucherman et al. |
| 6,238,397 B1 | 5/2001 | Zucherman et al. |
| 6,264,651 B1 | 7/2001 | Underwood et al. |
| 6,264,656 B1 | 7/2001 | Michelson |
| 6,267,765 B1 | 7/2001 | Taylor et al. |
| 6,270,498 B1 | 8/2001 | Michelson |
| 6,280,444 B1 | 8/2001 | Zucherman et al. |
| 6,312,431 B1 | 11/2001 | Asfora |
| 6,328,730 B1 | 12/2001 | Harkrider, Jr. |
| 6,332,882 B1 | 12/2001 | Zucherman et al. |
| 6,332,883 B1 | 12/2001 | Zucherman et al. |
| 6,336,930 B1 | 1/2002 | Stalcup et al. |
| 6,348,053 B1 | 2/2002 | Cachia |
| 6,364,883 B1 | 4/2002 | Santilli |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,387,130 B1 | 5/2002 | Stone et al. |
| 6,395,032 B1 | 5/2002 | Gauchet et al. |
| 6,402,740 B1 | 6/2002 | Ellis et al. |
| 6,402,750 B1 | 6/2002 | Atkinson et al. |
| 6,402,784 B1 | 6/2002 | Wardlaw et al. |
| 6,413,228 B1 | 7/2002 | Hung et al. |
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,443,988 B2 | 9/2002 | Felt et al. |

(56) References Cited

U.S. PATENT DOCUMENTS

| | | |
|---|---|---|
| 6,447,547 B1 | 9/2002 | Michelson |
| 6,451,019 B1 | 9/2002 | Zucherman et al. |
| 6,451,020 B1 | 9/2002 | Zucherman et al. |
| 6,464,682 B1 | 10/2002 | Snoke |
| 6,471,976 B1 | 10/2002 | Taylor et al. |
| 6,478,796 B2 | 11/2002 | Zucherman et al. |
| 6,478,822 B1 | 11/2002 | Leroux et al. |
| 6,500,178 B2 | 12/2002 | Zucherman et al. |
| 6,514,256 B2 | 2/2003 | Zucherman et al. |
| 6,530,925 B2 | 3/2003 | Boudard et al. |
| 6,558,333 B2 | 5/2003 | Gilboa et al. |
| 6,565,570 B2 | 5/2003 | Sterett et al. |
| 6,572,617 B1 | 6/2003 | Senegas et al. |
| 6,575,981 B1 | 6/2003 | Boyd et al. |
| 6,579,281 B2 | 6/2003 | Palmer et al. |
| 6,579,319 B2 | 6/2003 | Goble et al. |
| 6,582,433 B2 | 6/2003 | Yun |
| 6,582,451 B1 | 6/2003 | Marucci et al. |
| 6,599,292 B1 | 7/2003 | Ray |
| 6,602,248 B1 | 8/2003 | Sharps et al. |
| 6,610,065 B1 | 8/2003 | Branch et al. |
| 6,610,091 B1 | 8/2003 | Reiley |
| 6,616,673 B1 | 9/2003 | Stone |
| 6,626,944 B1 | 9/2003 | Taylor et al. |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,663,637 B2 | 12/2003 | Dixon et al. |
| 6,679,886 B2 | 1/2004 | Weikel et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,702,847 B2 | 3/2004 | DiCarlo |
| 6,712,819 B2 | 3/2004 | Zucherman et al. |
| 6,716,215 B1 | 4/2004 | David et al. |
| 6,716,245 B2 | 4/2004 | Pasquet et al. |
| 6,726,690 B2 | 4/2004 | Eckman |
| 6,733,534 B2 | 5/2004 | Sherman |
| 6,746,485 B1 | 6/2004 | Zucherman et al. |
| 6,761,720 B1 | 7/2004 | Senegas et al. |
| 6,783,529 B2 | 8/2004 | Hover et al. |
| 6,783,546 B2 | 8/2004 | Zucherman et al. |
| 6,796,983 B1 | 9/2004 | Zucherman et al. |
| 6,805,697 B1 | 10/2004 | Helm et al. |
| 6,835,205 B2 | 12/2004 | Atkinson et al. |
| 6,840,944 B2 | 1/2005 | Suddaby |
| 6,858,029 B2 | 2/2005 | Yeh |
| 6,869,398 B2 | 3/2005 | Obenchain et al. |
| 6,875,212 B2 | 4/2005 | Shaolian et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Arnin et al. |
| 6,974,478 B2 | 12/2005 | Reiley et al. |
| 7,011,685 B2 | 3/2006 | Arnin et al. |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,179,225 B2 | 2/2007 | Shluzas et al. |
| 7,187,064 B2 | 3/2007 | Tzu et al. |
| 7,189,234 B2 | 3/2007 | Zucherman et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |
| 7,223,289 B2 | 5/2007 | Trieu et al. |
| 7,229,441 B2 | 6/2007 | Trieu et al. |
| 7,238,204 B2 | 7/2007 | Le Couedic et al. |
| 7,252,673 B2 | 8/2007 | Lim |
| 7,273,496 B2 | 9/2007 | Mitchell |
| 7,282,063 B2 | 10/2007 | Cohen et al. |
| 7,297,162 B2 | 11/2007 | Mujwid |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,390,330 B2 | 6/2008 | Harp |
| 7,410,501 B2 | 8/2008 | Michelson |
| 7,442,208 B2 | 10/2008 | Mathieu et al. |
| 7,445,637 B2 | 11/2008 | Taylor |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,510,567 B2 | 3/2009 | Zucherman et al. |
| 7,520,887 B2 | 4/2009 | Maxy et al. |
| 7,520,899 B2 | 4/2009 | Zucherman et al. |
| 7,547,308 B2 | 6/2009 | Bertagnoli et al. |
| 7,549,999 B2 | 6/2009 | Zucherman et al. |
| 7,550,009 B2 | 6/2009 | Arnin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,585,313 B2 | 9/2009 | Kwak et al. |
| 7,585,316 B2 | 9/2009 | Trieu |
| 7,588,588 B2 | 9/2009 | Spitler et al. |
| 7,591,851 B2 | 9/2009 | Winslow et al. |
| 7,601,170 B2 | 10/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,950 B2 | 12/2009 | Baccelli et al. |
| 7,658,752 B2 | 2/2010 | Labrom et al. |
| 7,662,187 B2 | 2/2010 | Zucherman et al. |
| 7,666,186 B2 | 2/2010 | Harp |
| 7,666,209 B2 | 2/2010 | Zucherman et al. |
| 7,666,228 B2 | 2/2010 | Le Couedic et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,695,513 B2 | 4/2010 | Zucherman et al. |
| 7,699,852 B2 | 4/2010 | Frankel et al. |
| 7,699,873 B2 | 4/2010 | Stevenson et al. |
| D618,796 S | 6/2010 | Cantu et al. |
| 7,727,233 B2 | 6/2010 | Blackwell et al. |
| 7,727,241 B2 | 6/2010 | Gorensek et al. |
| 7,731,751 B2 | 6/2010 | Butler et al. |
| 7,742,795 B2 | 6/2010 | Stone et al. |
| 7,749,231 B2 | 7/2010 | Bonvallet et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,758,647 B2 | 7/2010 | Arnin et al. |
| 7,763,028 B2 | 7/2010 | Lim et al. |
| 7,763,050 B2 | 7/2010 | Winslow et al. |
| 7,763,051 B2 | 7/2010 | Labrom et al. |
| 7,763,073 B2 | 7/2010 | Hawkins et al. |
| 7,763,074 B2 | 7/2010 | Altarac et al. |
| 7,766,967 B2 | 8/2010 | Francis |
| 7,776,090 B2 | 8/2010 | Winslow et al. |
| 7,780,709 B2 | 8/2010 | Bruneau et al. |
| 7,789,898 B2 | 9/2010 | Peterman |
| 7,794,476 B2 | 9/2010 | Wisnewski |
| 7,803,190 B2 | 9/2010 | Zucherman et al. |
| 7,806,911 B2 | 10/2010 | Peckham |
| 7,811,308 B2 | 10/2010 | Arnin et al. |
| 7,811,322 B2 | 10/2010 | Arnin et al. |
| 7,811,323 B2 | 10/2010 | Arnin et al. |

(56) References Cited

U.S. PATENT DOCUMENTS

| | | |
|---|---|---|
| 7,811,324 B2 | 10/2010 | Arnin et al. |
| 7,811,330 B2 | 10/2010 | Arnin et al. |
| 7,819,921 B2 | 10/2010 | Grotz |
| 7,828,822 B2 | 11/2010 | Zucherman et al. |
| 7,828,849 B2 | 11/2010 | Lim |
| 7,833,272 B2 | 11/2010 | Arnin et al. |
| 7,837,687 B2 | 11/2010 | Harp |
| 7,837,688 B2 | 11/2010 | Boyer, II et al. |
| 7,837,700 B2 | 11/2010 | Harp |
| 7,837,711 B2 | 11/2010 | Bruneau et al. |
| 7,837,734 B2 | 11/2010 | Zucherman et al. |
| 7,846,183 B2 | 12/2010 | Blain |
| 7,846,185 B2 | 12/2010 | Carls et al. |
| 7,846,186 B2 | 12/2010 | Taylor |
| 7,857,815 B2 | 12/2010 | Zucherman et al. |
| 7,862,569 B2 | 1/2011 | Zucherman et al. |
| 7,862,586 B2 | 1/2011 | Malek |
| 7,862,590 B2 | 1/2011 | Lim et al. |
| 7,862,592 B2 | 1/2011 | Peterson et al. |
| 7,862,615 B2 | 1/2011 | Carli et al. |
| 7,867,276 B2 | 1/2011 | Matge et al. |
| 7,871,426 B2 | 1/2011 | Chin et al. |
| 7,896,879 B2 | 3/2011 | Solsberg et al. |
| 7,942,830 B2 | 5/2011 | Solsberg et al. |
| 7,955,392 B2 | 6/2011 | Dewey et al. |
| 7,985,246 B2 * | 7/2011 | Trieu ............... A61B 17/7065 606/249 |
| 8,012,207 B2 | 9/2011 | Kim |
| 8,025,684 B2 | 9/2011 | Garcia-Bengochea et al. |
| 8,057,513 B2 | 11/2011 | Kohm et al. |
| 8,062,332 B2 | 11/2011 | Cunningham et al. |
| 8,100,823 B2 | 1/2012 | Harp |
| 8,123,782 B2 | 2/2012 | Altarac et al. |
| 8,123,807 B2 | 2/2012 | Kim |
| 8,128,662 B2 | 3/2012 | Altarac et al. |
| 8,152,837 B2 | 4/2012 | Altarac et al. |
| 8,167,944 B2 | 5/2012 | Kim |
| 8,226,690 B2 | 7/2012 | Altarac et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,317,864 B2 | 11/2012 | Kim |
| 8,409,282 B2 | 4/2013 | Kim |
| 8,425,559 B2 | 4/2013 | Tebbe et al. |
| 8,608,762 B2 | 12/2013 | Solsberg et al. |
| 8,613,747 B2 | 12/2013 | Altarac et al. |
| 8,628,574 B2 | 1/2014 | Altarac et al. |
| 8,696,671 B2 | 4/2014 | Solsberg et al. |
| 8,734,477 B2 | 5/2014 | Solsberg et al. |
| 8,740,948 B2 | 6/2014 | Reglos et al. |
| 8,845,726 B2 | 9/2014 | Tebbe et al. |
| 8,864,828 B2 | 10/2014 | Altarac et al. |
| 8,882,772 B2 | 11/2014 | Solsberg et al. |
| 8,894,653 B2 | 11/2014 | Solsberg et al. |
| 8,900,271 B2 | 12/2014 | Kim |
| 8,945,183 B2 | 2/2015 | Altarac et al. |
| 9,023,084 B2 | 5/2015 | Kim |
| 9,039,742 B2 | 5/2015 | Altarac et al. |
| 9,119,680 B2 | 9/2015 | Altarac et al. |
| 9,125,692 B2 | 9/2015 | Kim |
| 9,155,570 B2 | 10/2015 | Altarac et al. |
| 9,155,572 B2 | 10/2015 | Altarac et al. |
| 9,161,783 B2 | 10/2015 | Altarac et al. |
| 9,186,186 B2 | 11/2015 | Reglos et al. |
| 9,211,146 B2 | 12/2015 | Kim |
| 9,283,005 B2 | 3/2016 | Tebbe et al. |
| 9,314,279 B2 | 4/2016 | Kim |
| 9,393,055 B2 | 7/2016 | Altarac et al. |
| 2001/0031965 A1 | 10/2001 | Zucherman et al. |
| 2002/0022856 A1 | 2/2002 | Johnson |
| 2002/0042607 A1 | 4/2002 | Palmer et al. |
| 2002/0143331 A1 | 10/2002 | Zucherman et al. |
| 2003/0040746 A1 | 2/2003 | Mitchell et al. |
| 2003/0040753 A1 | 2/2003 | Daum et al. |
| 2003/0074075 A1 | 4/2003 | Thomas et al. |
| 2003/0149438 A1 | 8/2003 | Nichols et al. |
| 2003/0153976 A1 | 8/2003 | Cauthen et al. |
| 2003/0176921 A1 | 9/2003 | Lawson |
| 2003/0220643 A1 | 11/2003 | Ferree |
| 2003/0220650 A1 | 11/2003 | Major et al. |
| 2003/0233098 A1 | 12/2003 | Markworth |
| 2004/0087947 A1 | 5/2004 | Lim et al. |
| 2004/0106997 A1 | 6/2004 | Lieberson |
| 2004/0106999 A1 | 6/2004 | Mathews |
| 2004/0167625 A1 | 8/2004 | Beyar et al. |
| 2004/0220568 A1 | 11/2004 | Zucherman et al. |
| 2005/0049708 A1 | 3/2005 | Atkinson et al. |
| 2005/0075634 A1 | 4/2005 | Zucherman et al. |
| 2005/0090822 A1 | 4/2005 | DiPoto |
| 2005/0101955 A1 | 5/2005 | Zucherman et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0192586 A1 | 9/2005 | Zucherman et al. |
| 2005/0192671 A1 | 9/2005 | Bao et al. |
| 2005/0209603 A1 | 9/2005 | Zucherman et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0245937 A1 | 11/2005 | Winslow |
| 2005/0261768 A1 | 11/2005 | Trieu |
| 2005/0278036 A1 | 12/2005 | Leonard et al. |
| 2006/0036258 A1 | 2/2006 | Zucherman et al. |
| 2006/0064165 A1 | 3/2006 | Zucherman et al. |
| 2006/0064166 A1 | 3/2006 | Zucherman et al. |
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0102269 A1 | 5/2006 | Uchida et al. |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0195102 A1 | 8/2006 | Malandain |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0241597 A1 | 10/2006 | Mitchell et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271044 A1 | 11/2006 | Petrini et al. |
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1 | 11/2006 | Zucherman et al. |
| 2006/0276801 A1 | 12/2006 | Yerby et al. |
| 2006/0276897 A1 | 12/2006 | Winslow et al. |
| 2006/0282077 A1 | 12/2006 | Labrom et al. |
| 2006/0282078 A1 | 12/2006 | Labrom et al. |
| 2007/0016196 A1 | 1/2007 | Winslow et al. |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0100340 A1 | 5/2007 | Lange et al. |
| 2007/0100366 A1 | 5/2007 | Dziedzic et al. |
| 2007/0123863 A1 | 5/2007 | Winslow et al. |
| 2007/0123904 A1 | 5/2007 | Stad et al. |

(56) References Cited

U.S. PATENT DOCUMENTS

| | | |
|---|---|---|
| 2007/0161991 A1 | 7/2007 | Altarac et al. |
| 2007/0161993 A1 | 7/2007 | Lowery et al. |
| 2007/0173818 A1 | 7/2007 | Hestad et al. |
| 2007/0173821 A1 | 7/2007 | Trieu |
| 2007/0173822 A1 | 7/2007 | Bruneau et al. |
| 2007/0173823 A1 | 7/2007 | Dewey et al. |
| 2007/0173832 A1 | 7/2007 | Tebbe et al. |
| 2007/0173939 A1 | 7/2007 | Kim et al. |
| 2007/0179500 A1 | 8/2007 | Chin et al. |
| 2007/0185490 A1 | 8/2007 | Implicito |
| 2007/0191948 A1 | 8/2007 | Arnin et al. |
| 2007/0191991 A1 | 8/2007 | Addink |
| 2007/0198045 A1 | 8/2007 | Morton et al. |
| 2007/0198091 A1 | 8/2007 | Boyer et al. |
| 2007/0203493 A1 | 8/2007 | Zucherman et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208345 A1 | 9/2007 | Marnay et al. |
| 2007/0208346 A1 | 9/2007 | Marnay et al. |
| 2007/0208366 A1 | 9/2007 | Pellegrino et al. |
| 2007/0210018 A1 | 9/2007 | Wallwiener et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0225814 A1 | 9/2007 | Atkinson et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0265626 A1 | 11/2007 | Seme |
| 2007/0270822 A1 | 11/2007 | Heinz |
| 2007/0270823 A1 | 11/2007 | Trieu et al. |
| 2007/0270824 A1 | 11/2007 | Lim et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276390 A1 | 11/2007 | Solsberg et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2008/0015700 A1 | 1/2008 | Zucherman et al. |
| 2008/0021468 A1 | 1/2008 | Zucherman et al. |
| 2008/0021560 A1 | 1/2008 | Zucherman et al. |
| 2008/0021561 A1 | 1/2008 | Zucherman et al. |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051896 A1 | 2/2008 | Suddaby |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071378 A1 | 3/2008 | Zucherman et al. |
| 2008/0071380 A1 | 3/2008 | Sweeney |
| 2008/0086212 A1 | 4/2008 | Zucherman et al. |
| 2008/0108990 A1 | 5/2008 | Mitchell et al. |
| 2008/0114455 A1 | 5/2008 | Lange et al. |
| 2008/0132952 A1 | 6/2008 | Malandain et al. |
| 2008/0167655 A1 | 7/2008 | Wang et al. |
| 2008/0167656 A1 | 7/2008 | Zucherman et al. |
| 2008/0172057 A1 | 7/2008 | Zucherman et al. |
| 2008/0177272 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0183210 A1 | 7/2008 | Zucherman et al. |
| 2008/0188895 A1 | 8/2008 | Cragg et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234708 A1 | 9/2008 | Houser et al. |
| 2008/0234824 A1 | 9/2008 | Youssef et al. |
| 2008/0288075 A1 | 11/2008 | Zucherman et al. |
| 2008/0319550 A1 | 12/2008 | Altarac et al. |
| 2009/0012528 A1 | 1/2009 | Aschmann et al. |
| 2009/0118833 A1 | 5/2009 | Hudgins et al. |
| 2009/0125030 A1 | 5/2009 | Tebbe et al. |
| 2009/0125036 A1 | 5/2009 | Bleich |
| 2009/0138046 A1 | 5/2009 | Altarac et al. |
| 2009/0138055 A1 | 5/2009 | Altarac et al. |
| 2009/0222043 A1 | 9/2009 | Altarac et al. |
| 2009/0248079 A1 | 10/2009 | Kwak et al. |
| 2009/0292315 A1 | 11/2009 | Trieu |
| 2010/0042217 A1 | 2/2010 | Zucherman et al. |
| 2010/0082108 A1 | 4/2010 | Zucherman et al. |
| 2010/0114100 A1 | 5/2010 | Mehdizade |
| 2010/0131009 A1 | 5/2010 | Roebling et al. |
| 2010/0228092 A1 | 9/2010 | Ortiz et al. |
| 2010/0234889 A1 | 9/2010 | Hess |
| 2010/0262243 A1 | 10/2010 | Zucherman et al. |
| 2010/0280551 A1 | 11/2010 | Pool et al. |
| 2010/0305611 A1 | 12/2010 | Zucherman et al. |
| 2011/0245833 A1 | 10/2011 | Anderson |
| 2011/0313457 A1 | 12/2011 | Reglos et al. |
| 2012/0078301 A1 | 3/2012 | Hess |
| 2012/0158063 A1 | 6/2012 | Altarac et al. |
| 2012/0226315 A1 | 9/2012 | Altarac et al. |
| 2012/0232552 A1 | 9/2012 | Morgenstern Lopez et al. |
| 2012/0303039 A1 | 11/2012 | Chin et al. |
| 2012/0330359 A1 | 12/2012 | Kim |
| 2013/0012998 A1 | 1/2013 | Altarac et al. |

(56) References Cited

U.S. PATENT DOCUMENTS

| | | |
|---|---|---|
| 2013/0072985 A1 | 3/2013 | Kim |
| 2013/0150886 A1 | 6/2013 | Altarac et al. |
| 2013/0165974 A1 | 6/2013 | Kim |
| 2013/0165975 A1 | 6/2013 | Tebbe et al. |
| 2013/0172932 A1 | 7/2013 | Altarac et al. |
| 2013/0172933 A1 | 7/2013 | Altarac et al. |
| 2013/0289399 A1 | 10/2013 | Choi et al. |
| 2013/0289622 A1 | 10/2013 | Kim |
| 2014/0081332 A1 | 3/2014 | Altarac et al. |
| 2014/0214082 A1 | 7/2014 | Reglos et al. |
| 2014/0228884 A1 | 8/2014 | Altarac et al. |
| 2014/0275992 A1 | 9/2014 | Choi et al. |
| 2015/0150598 A1 | 6/2015 | Tebbe et al. |
| 2015/0150604 A1 | 6/2015 | Kim |
| 2015/0164560 A1 | 6/2015 | Altarac et al. |
| 2015/0374415 A1 | 12/2015 | Kim |
| 2016/0030092 A1 | 2/2016 | Altarac et al. |
| 2016/0045232 A1 | 2/2016 | Altarac et al. |
| 2016/0135853 A1 | 5/2016 | Altarac et al. |
| 2016/0248222 A1 | 8/2016 | Miyata |
| 2016/0317193 A1 | 11/2016 | Kim et al. |
| 2017/0071588 A1 | 3/2017 | Choi |
| 2017/0128110 A1 | 5/2017 | Altarac et al. |

FOREIGN PATENT DOCUMENTS

| | | |
|---|---|---|
| CN | 101897603 | 12/2010 |
| DE | 69507480 | 9/1999 |
| EP | 322334 | 6/1989 |
| EP | 0767636 | 4/1997 |
| EP | 0768843 B1 | 4/1997 |
| EP | 0959792 B1 | 12/1999 |
| EP | 1027004 A1 | 8/2000 |
| EP | 1030615 A1 | 8/2000 |
| EP | 1138268 | 10/2001 |
| EP | 1330987 A1 | 7/2003 |
| EP | 1056408 B1 | 12/2003 |
| EP | 1343424 B1 | 9/2004 |
| EP | 1454589 A1 | 9/2004 |
| EP | 1148850 B1 | 4/2005 |
| EP | 1570793 A2 | 9/2005 |
| EP | 1299042 B1 | 3/2006 |
| EP | 1578314 B1 | 5/2007 |
| EP | 1675535 B1 | 5/2007 |
| EP | 1861046 A2 | 12/2007 |
| FR | 2681525 A1 | 3/1993 |
| FR | 2722980 A1 | 2/1996 |
| FR | 2816197 A1 | 5/2002 |
| FR | 2884136 A1 | 10/2006 |
| FR | 2888744 A1 | 1/2007 |
| SU | 988281 A1 | 1/1983 |
| WO | WO-9404088 A1 | 3/1994 |
| WO | WO-9426192 A1 | 11/1994 |
| WO | WO-9525485 A1 | 9/1995 |
| WO | WO-9531158 A1 | 11/1995 |
| WO | WO-9600049 A1 | 1/1996 |
| WO | WO-9829047 A1 | 7/1998 |
| WO | WO-9921500 A1 | 5/1999 |
| WO | WO-9921501 A1 | 5/1999 |
| WO | WO-9942051 A1 | 8/1999 |
| WO | WO-0013619 A1 | 3/2000 |
| WO | WO-0044319 A1 | 8/2000 |
| WO | WO-0044321 A2 | 8/2000 |
| WO | WO-0128442 A1 | 4/2001 |
| WO | WO-0191657 A1 | 12/2001 |
| WO | WO-0191658 A1 | 12/2001 |
| WO | WO-0203882 A2 | 1/2002 |
| WO | WO-0207623 A1 | 1/2002 |
| WO | WO-0207624 A1 | 1/2002 |
| WO | WO-02051326 A1 | 7/2002 |
| WO | WO-02067793 A2 | 9/2002 |
| WO | WO-02071960 A1 | 9/2002 |
| WO | WO-02076336 A2 | 10/2002 |
| WO | WO-03007791 A2 | 1/2003 |
| WO | WO-03007829 A1 | 1/2003 |
| WO | WO-03008016 A2 | 1/2003 |
| WO | WO-03015646 A2 | 2/2003 |
| WO | WO-03024298 A2 | 3/2003 |
| WO | WO-03045262 A2 | 6/2003 |
| WO | WO-03099147 A1 | 12/2003 |
| WO | WO-03101350 A1 | 12/2003 |
| WO | WO-2004073533 A1 | 9/2004 |
| WO | WO-2004110300 A2 | 12/2004 |
| WO | WO-2005009300 A1 | 2/2005 |
| WO | WO-2005013839 A2 | 2/2005 |
| WO | WO-2005025461 A2 | 3/2005 |
| WO | WO-2005041799 A1 | 5/2005 |
| WO | WO-2005044152 A1 | 5/2005 |
| WO | WO-2005055868 A2 | 6/2005 |
| WO | WO-2005079672 A2 | 9/2005 |
| WO | WO-2005086776 A2 | 9/2005 |
| WO | WO-2005115261 A1 | 12/2005 |
| WO | WO-2006033659 A2 | 3/2006 |
| WO | WO-2006034423 A2 | 3/2006 |
| WO | WO-2006039243 | 4/2006 |
| WO | WO-2006039260 A2 | 4/2006 |
| WO | WO-2006045094 A2 | 4/2006 |
| WO | WO-2006063047 A2 | 6/2006 |
| WO | WO-2006064356 A1 | 6/2006 |
| WO | WO-2006065774 A1 | 6/2006 |
| WO | WO-2006089085 A2 | 8/2006 |
| WO | WO-2006102269 A2 | 9/2006 |
| WO | WO-2006102428 A1 | 9/2006 |
| WO | WO-2006102485 A2 | 9/2006 |
| WO | WO-2006107539 A1 | 10/2006 |
| WO | WO-2006110462 A2 | 10/2006 |
| WO | WO-2006110464 A1 | 10/2006 |
| WO | WO-2006110767 A1 | 10/2006 |
| WO | WO-2006113080 A2 | 10/2006 |
| WO | WO-2006113406 A2 | 10/2006 |
| WO | WO-2006113814 A2 | 10/2006 |
| WO | WO-2006118945 A1 | 11/2006 |
| WO | WO-2006119235 A2 | 11/2006 |
| WO | WO-2006119236 A2 | 11/2006 |
| WO | WO-2006135511 A1 | 12/2006 |
| WO | WO-2007015028 A1 | 2/2007 |
| WO | WO-2007035120 A1 | 3/2007 |
| WO | WO-2007075375 A2 | 7/2007 |
| WO | WO-2007075788 A2 | 7/2007 |
| WO | WO-2007075791 A2 | 7/2007 |
| WO | WO-2007089605 A2 | 8/2007 |
| WO | WO-2007089905 A2 | 8/2007 |
| WO | WO-2007089975 A1 | 8/2007 |
| WO | WO-2007097735 A2 | 8/2007 |
| WO | WO-2007109402 A2 | 9/2007 |
| WO | WO-2007110604 A1 | 10/2007 |
| WO | WO-2007111795 A1 | 10/2007 |
| WO | WO-2007111979 A2 | 10/2007 |
| WO | WO-2007111999 A2 | 10/2007 |
| WO | WO-2007117882 A2 | 10/2007 |
| WO | WO-2007121070 A2 | 10/2007 |
| WO | WO-2007127550 A2 | 11/2007 |
| WO | WO-2007127588 A1 | 11/2007 |
| WO | WO-2007127677 A1 | 11/2007 |
| WO | WO-2007127689 A2 | 11/2007 |
| WO | WO-2007127694 A2 | 11/2007 |
| WO | WO-2007127734 A2 | 11/2007 |
| WO | WO-2007127736 A2 | 11/2007 |
| WO | WO-2007131165 A2 | 11/2007 |
| WO | WO-2007134113 A2 | 11/2007 |
| WO | WO-2008009049 A1 | 1/2008 |
| WO | WO-2008048645 A2 | 4/2008 |
| WO | WO-2008057506 A2 | 5/2008 |
| WO | WO-2008130564 A1 | 10/2008 |
| WO | WO-2009014728 A2 | 1/2009 |
| WO | WO-2009033093 A1 | 3/2009 |
| WO | WO-2009086010 A2 | 7/2009 |
| WO | WO-2009091922 A2 | 7/2009 |
| WO | WO-2009094463 A2 | 7/2009 |
| WO | WO-2009114479 A2 | 9/2009 |

(56) References Cited

FOREIGN PATENT DOCUMENTS

| WO | WO-2011084477 A2 | 7/2011 |
|---|---|---|
| WO | WO-2015171814 A1 | 11/2015 |

OTHER PUBLICATIONS

International Search Report and Written Opinion; Application No. PCT/US2005/038026; dated Apr. 22, 2008, 9 pages.
International Search Report and Written Opinion; Application No. PCT/US2005/044256; dated Jul. 28, 2006, 7 pages.
International Search Report and Written Opinion; Application No. PCT/US2006/047824; dated Oct. 16, 2008, 17 pages.
International Search Report and Written Opinion; Application No. PCT/US2006/048611; dated Oct. 14, 2008; 10 pages.
International Search Report and Written Opinion; Application No. PCT/US2006/048614; dated Feb. 3, 2006; 23 pages.
International Search Report and Written Opinion; Application No. PCT/US2007/022171; dated Apr. 15, 2008, 9 pages.
International Search Report and Written Opinion; Application No. PCT/US2007/023312; dated May 22, 2008, 14 pages.
International Search Report and Written Opinion; Application No. PCT/US2008/004901; dated Aug. 19, 2008, 7 pages.
International Search Report and Written Opinion; Application No. PCT/US2008/008382; dated Mar. 2, 2009, 13 pages.
International Search Report and Written Opinion; Application No. PCT/US2008/008983; dated Feb. 23, 2009, 7 pages.
International Search Report and Written Opinion; Application No. PCT/US2008/075487; dated Dec. 31, 2008, 7 pages.
International Search Report and Written Opinion; Application No. PCT/US2008/087527; dated Jul. 30, 2009, 10 pages.
International Search Report and Written Opinion; Application No. PCT/US2009/031150; dated Aug. 28, 2009, 6 pages.
International Search Report and Written Opinion; Application No. PCT/US2009/036561; dated Sep. 17, 2009, 12 pages.
Minns, R.J., et al., "Preliminary Design and Experimental Studies of a Noval Soft Implant for Correcting Sagittal Plane Instability in the Lumbar Spine," (1997) Spine, 22(16): 1819-1827.
Supplementary European Search Report; Application No. EP05849654.6; Applicant: Vertiflex, Inc.; Date of Completion: May 15, 2009, 10 pages.
Supplementary European Search Report; Application No. EP07861426.0; Applicant: Vertiflex, Inc.; Date of Completion: Jun. 7, 2011, 6 pages.
Supplementary European Search Report; Application No. EP07861721.4; Applicant: Vertiflex, Inc.; Date of Completion: Nov. 24, 2009, 6 pages.
Supplementary European Search Report; Application No. EP09170304.1; Applicant: Vertiflex, Inc.; Date of Completion: Nov. 11, 2009, 5 pages.
Supplementary European Search Report; Application No. EP09170338.9; Applicant: Vertiflex, Inc.; Date of Completion: Nov. 12, 2009, 6 pages.
Supplementary European Search Report; Application No. EP09702116.6; Applicant: Vertiflex, Inc.; Date of Completion: Feb. 11, 2011, 6 pages.
Supplementary European Search Report; Application No. EP11151901.3; Applicant: Vertiflex, Inc.; Date of Completion: Apr. 7, 2011, 6 pages.
Swan, Colby, "Preliminary Design and Experimental Studies of a Novel Soft Implant for Correcting Sogittal Plane Instability in the Lumbar Spine," Spine, 1997, 22(16), 1826-1827.
Australia Exam Report for Application No. AU2008296066, Applicant: VertiFlex, Inc.; dated Mar. 6, 2013, 3 pages.
Canada Exam Report for Application No. CA2698718, Applicant: Vertiflex, Inc.; dated May 20, 2014, 3 pages.
Supplementary European Search Report for Application No. EP08799267.3; Applicant: VertiFlex, Inc.; dated Jun. 29, 2011, 7 pages.
International Search Report and Written Opinion; Application No. PCT/US2010/060498; dated Aug. 25, 2011, 17 pages.
International Search Report and Written Opinion; Application No. PCT/US2009/031710; dated Sep. 1, 2009, 10 pages.
International Search Report, counterpart PCT Application PCT/US2013/038534, Applicant: Vertiflex, Inc., Aug. 7, 2013, 16 pages.
McCulloch, John A., Young, Paul H., "Essentials of Spinal Microsurgery," 1998, pp. 453-485. Lippincott-Raven Publishers, Philadelphia, PA (37 pages total).
Lee, Seungcheol et al., "New Surgical Techniques of Percutaneous Endoscopic Lumbar Disectomy for Migrated Disc Herniation," Joint Dis. Rel. Surg., 16(2); pp. 102-110 (2005).
Choi, Gun et al., "Percutaneous Endoscopic Interlaminar Disectomy for Intracanalicular Disc Herniations at L5-S1 Using a Rigid Working Channel Endoscope," Operative Neurosurg., 58: pp. 59-68 (2006).
Lee, Seungcheol et al., "Percutaneous Endoscopic Interlaminar Disectomy for L5-S1 Disc Herniation: Axillary Approach and Preliminary Results," J. of Korean Neurosurg. Soc., 40: pp. 19-83 (2006).
Decision on Petition in U.S. Appl. No. 60/592,099, May 4, 2005.
Vaccaro, Alexander J. et al., MasterCases Spine Surgery, 2001, pp. 100-107. Thieme Medical Publishers, Inc., NY. (10 pages total).
Fast, Avital et al., "Surgical Treatment of Lumbar Spinal Stenosis in the Elderly," Arch Phys. Med Rehabil., Mar. 1985, pp. 149-151, vol. 66.
Palmer, Sylvain et al., "Bilateral decompressive surgery in lumbar spinal stenosis associated with spondylolisthesis: unilateral approach and use of a microscope and tubular retractor system," Neurosurgery Focus, Jul. 2002, pp. 1-6, vol. 13.
International Search Report and Written Opinion; Application No. PCT/US2009/029537; Applicant: Vertiflex, Inc. dated Aug. 3, 2015, 14 pages.
Australia Exam Report for Application No. AU2014203394, Applicant: VertiFlex, Inc.; dated Mar. 15, 2016, 2 pages.
European Further Exam Report for Application No. EP09702116.6; Applicant: VertiFlex, Inc.; dated Jul. 4, 2016, 4 pages.
European Examination Report for Application No. 08794704.0; Applicant: Vertiflex, Inc.; dated Apr. 5, 2017, 6 pages.
First Examination Report in European Patent Application No. 08780034.8, dated Jan. 16, 2017, 5 pages.

* cited by examiner

INTERSPINOUS SPACER

CROSS-REFERENCE TO RELATED APPLICATIONS

This application is a divisional of U.S. patent application Ser. No. 13/406,442, now U.S. Pat. No. 9,119,680, "Interspinous Spacer," filed on Feb. 27, 2012, which is a continuation of U.S. patent application Ser. No. 12/205,511, now U.S. Pat. No. 8,123,782, entitled "Interspinous Spacer," filed on Sep. 5, 2008, which claims priority to and the benefit of U.S. Provisional Patent Application No. 60/967,805 entitled "Interspinous spacer," filed on Sep. 7, 2007, all of which are hereby incorporated by reference in their entireties. U.S. Pat. No. 8,123,782 also claims priority to and is a continuation-in-part of U.S. patent application Ser. No. 12/220,427, now U.S. Pat. No. 8,277,488, entitled "Interspinous spacer," filed on Jul. 24, 2008 which is a non-provisional of U.S. Provisional Patent Application No. 60/961,741 entitled "Interspinous spacer," and filed on Jul. 24, 2007, and is a continuation-in-part of U.S. patent application Ser. No. 12/217,662, now U.S. Pat. No. 8,273,108, entitled "Interspinous spacer," filed on Jul. 8, 2008, which is a non-provisional of U.S. Provisional Patent Application No. 60/958,876 entitled "Interspinous spacer," filed on Jul. 9, 2007, and a continuation-in-part of U.S. patent application Ser. No. 12/148,104, now U.S. Pat. No. 8,292,922, entitled "Interspinous spacer," filed on Apr. 16, 2008, which is a non-provisional of U.S. Provisional Patent Application No. 60/923,971 entitled "Interspinous spacer," filed on Apr. 17, 2007, and U.S. Provisional Patent Application No. 60/923,841 entitled "Spacer insertion instrument," filed on Apr. 16, 2007, all of which are hereby incorporated by reference in their entireties. U.S. Pat. No. 8,123,782 is also a continuation-in-part of U.S. patent application Ser. No. 11/593,995, now U.S. Pat. No. 8,425,559, entitled "Systems and methods for posterior dynamic stabilization of the spine," filed on Nov. 7, 2006, which is a continuation-in-part of U.S. patent application Ser. No. 11/582,874, now U.S. Pat. No. 8,128,662, entitled "Minimally invasive tooling for delivery of interspinous spacer," filed on Oct. 18, 2006, which is a continuation-in-part of U.S. patent application Ser. No. 11/314,712, now U.S. Pat. No. 8,152,837, entitled "Systems and methods for posterior dynamic stabilization of the spine," filed on Dec. 20, 2005, which is a continuation-in-part of U.S. patent application Ser. No. 11/190,496, now U.S. Pat. No. 8,409,282, entitled "Systems and methods for posterior dynamic stabilization of the spine," filed on Jul. 26, 2005, which is a continuation-in-part of U.S. patent application Ser. No. 11/079,006, now U.S. Pat. No. 8,012,207, entitled "Systems and methods for posterior dynamic stabilization of the spine," filed on Mar. 10, 2005, which is a continuation-in-part of U.S. patent application Ser. No. 11/052,002, now U.S. Pat. No. 8,317,864, entitled "Systems and methods for posterior dynamic stabilization of the spine," filed on Feb. 4, 2005, which is a continuation-in-part of U.S. patent application Ser. No. 11/006,502, entitled "Systems and methods for posterior dynamic stabilization of the spine," filed on Dec. 6, 2004, now U.S. Pat. No. 8,123,807, which is a continuation-in-part of U.S. patent application Ser. No. 10/970,843, now U.S. Pat. No. 8,167,944, entitled "Systems and methods for posterior dynamic stabilization of the spine," filed on Oct. 20, 2004. All of the above-referenced applications and patents are hereby incorporated by reference in their entireties.

FIELD

The present invention generally relates to medical devices, in particular, implants for placement between adjacent spinous processes of a patient's spine.

BACKGROUND

With spinal stenosis, the spinal canal narrows and pinches the spinal cord and nerves, causing pain in the back and legs. Typically, with age, a person's ligaments may thicken, intervertebral discs may deteriorate and facet joints may break down—all contributing to the condition of the spine characterized by a narrowing of the spinal canal. Injury, heredity, arthritis, changes in blood flow and other causes may also contribute to spinal stenosis.

Doctors have been at the forefront with various treatments of the spine including medications, surgical techniques and implantable devices that alleviate and substantially reduce debilitating pain associated with the back. In one surgical technique, a spacer is implanted between adjacent spinous processes of a patient's spine. The implanted spacer opens the neural foramen, maintains the desired distance between vertebral body segments, and as a result, reduces impingement of nerves and relieves pain. For suitable candidates, an implantable interspinous spacer may provide significant benefits in terms of pain relief.

Any surgery is an ordeal. However, the type of device and how it is implanted has an impact. For example, one consideration when performing surgery to implant an interspinous spacer is the size of the incision that is required to allow introduction of the device. Small incisions and minimally invasive techniques are generally preferred as they affect less tissue and result in speedier recovery times. As such, there is a need for interspinous spacers that work well with surgical techniques that are minimally invasive and provide quick, easy and effective solutions for doctors and their patients. The present invention sets forth such a spacer.

SUMMARY

According to one aspect of the invention, an implantable spacer for placement between adjacent spinous processes is provided. The adjacent spinous processes includes a superior spinous process and an inferior spinous process. Each of the superior and inferior spinous processes has two lateral surfaces. The implantable spacer includes a body having a longitudinal axis. A wing is connected to the body and capable of movement with respect to the body. The wing has at least a first pair of extension members having longitudinal axes. The wing has at least one earning surface. The spacer further includes an actuator assembly connected to the body. The actuator assembly includes an actuator and a shaft connected to the actuator. The actuator assembly is configured such that the actuator is disposed inside the body such that the shaft is accessible at the proximal end of the spacer. The actuator is configured to move relative to the spacer body to contact the earning surface of the wing to move the wing from a first position to a second position.

According to another aspect of the invention, an implantable spacer for placement into an interspinous process space between adjacent spinous processes is provided. The adjacent spinous processes include a superior spinous process and an inferior spinous process. The implantable spacer includes a body having longitudinal axis, a first end and a second end. The first end is configured to be positioned inside the interspinous process space proximally to the spinal canal relative to the second end. The spacer further includes at least one movable element and a mechanism for moving the at least one movable element from a first position to a second position. The at least one movable element is configured to laterally stabilize the spacer relative to at least one of the superior or inferior spinous process when in said second position. The mechanism is configured such that movement of the at least one movable element from the first position to the second position is effected by moving the mechanism relative to the spacer body in a direction away from spinal canal.

According to another aspect of the invention, an implantable spacer for placement into an interspinous process space between adjacent spinous processes is provided. The adjacent spinous processes include a superior spinous process and an inferior spinous process. The implantable spacer includes a body having longitudinal axis, a first end and a second end. The first end is configured to be positioned inside the interspinous process space proximally to the spinal canal relative to the second end. The spacer further includes at least one movable element. The spacer also includes an actuator assembly connected to the body. The actuator assembly includes an actuator mechanism for moving the at least one element from a first position to a second position. The at least one movable element is configured to laterally stabilize the spacer relative to at least one of the superior or inferior spinous processes when in said second position. The spacer includes a locking mechanism for locking the at least one movable element in said second position. The locking mechanism includes a body link having at least one outer surface angled with respect to the longitudinal axis and configured such that effecting movement of the at least one element from a first position to a second position moves the body link relative to the body to create a force to lock the at least one movable element in place.

According to another aspect of the invention, an implantable spacer for placement into an interspinous process space between adjacent spinous processes is provided. The adjacent spinous processes include a superior spinous process and an inferior spinous process. The implantable spacer includes a spacer body and movable wing combination. The movable wing has a first position and a second position and at least one extension member for laterally stabilizing the spacer body with respect to the at least one spinous process when in said second position. The at least one extension member shares the length of the spacer body when in said first position.

According to another aspect of the invention, an implantable spacer for placement into an interspinous process space between adjacent spinous processes is provided. The adjacent spinous processes include a superior spinous process and an inferior spinous process. The implantable spacer includes a body having longitudinal axis, a first end and a second end. The body has a superior spinous process engaging surface and an inferior spinous process engaging surface. The spacer includes at least one movable element and an actuator assembly. The actuator assembly is connected to the body and configured for moving the at least one movable element from a first position to a second position. The at least one movable element is configured to laterally stabilize the spacer relative to at least one of the superior or inferior spinous processes when in said second position. When in the second position, the spacer is positionable within the interspinous process space such that the superior spinous process engaging surface faces the superior spinous process and the inferior spinous process engaging surface faces the inferior spinous process. The spacer is configured to abut at least one of the superior spinous process and inferior spinous process on a corresponding superior spinous process engaging surface and inferior spinous process engaging surface at a location along the body that is outside the location of the movable element when in the second position.

BRIEF DESCRIPTION OF THE DRAWINGS

The invention is best understood from the following detailed description when mad in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screws and equivalents thereof known to those skilled in the art, and so forth.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention is described in the accompanying figures and text as understood by a person having ordinary skill in the field of spinal implants and implant delivery instrumentation.

Figure 1B:
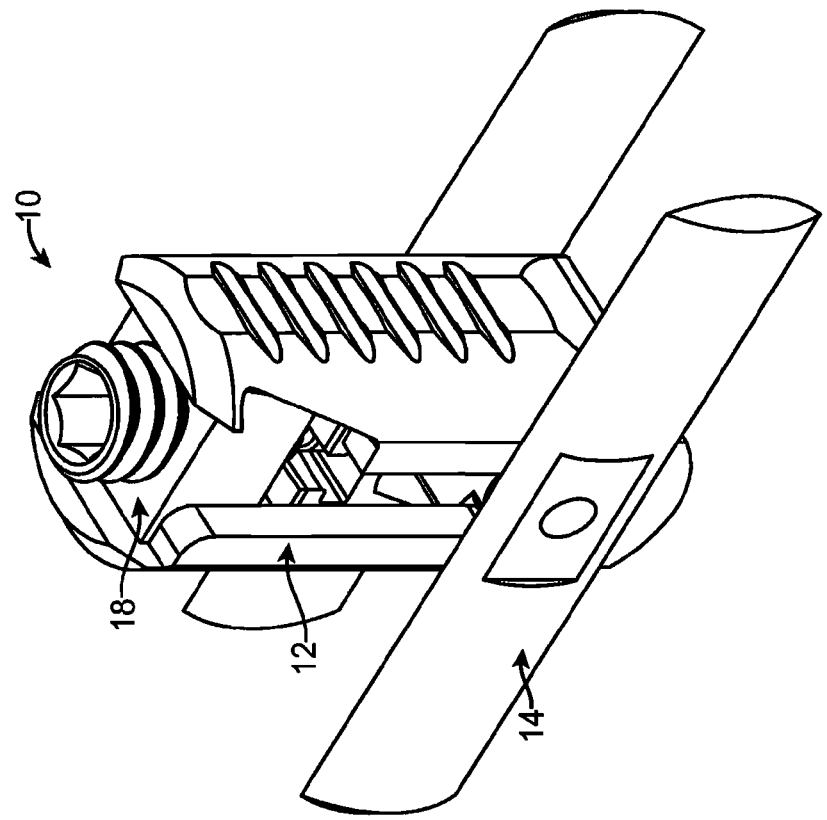
FIG. 1b illustrates a perspective view of a spacer in a deployed configuration according to the present invention.
Figure 1A:
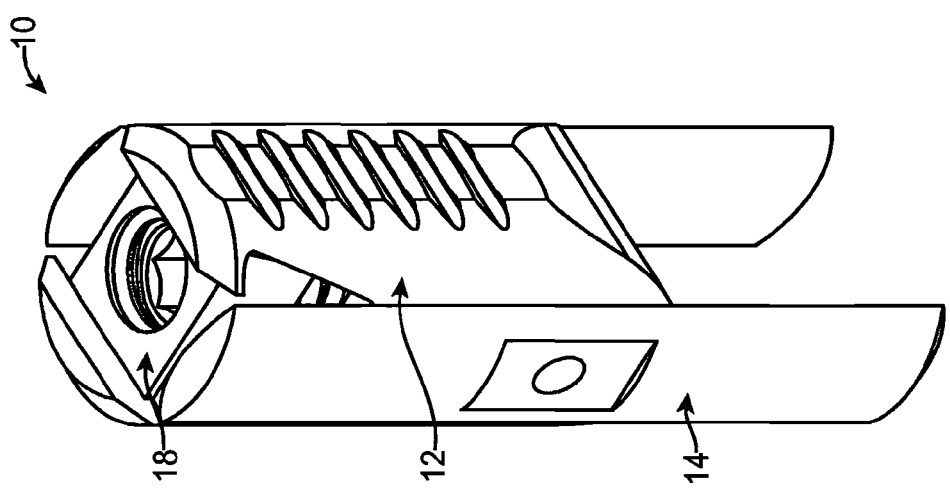
FIG. 1a illustrates a perspective view of a spacer in an undeployed configuration according to the present invention.

With reference to FIGS. 1a and 1b, a spacer 10 according to the present invention is shown. FIG. 1a illustrates the spacer 10 in a first position or undeployed configuration and FIG. 1b illustrates the spacer 10 in a second position or deployed configuration. The spacer 10 includes a body 12, an extension member, wing or arm 14, and an actuator assembly 18. The wing 14 and the actuator assembly 18 are connected to the body 12. When in the undeployed configuration shown in FIG. 1a, the longitudinal axis of the wing 14 is substantially parallel to the longitudinal axis of the body 12 whereas when in the deployed configuration shown in FIG. 1b, the wing 14 is substantially perpendicular to the longitudinal axis of the body 12. As seen in FIG. 1a, a portion of the wing 14 overlaps or shares a length of the body 12, thereby, advantageously reducing the length of the overall spacer 10.

Figure 2:
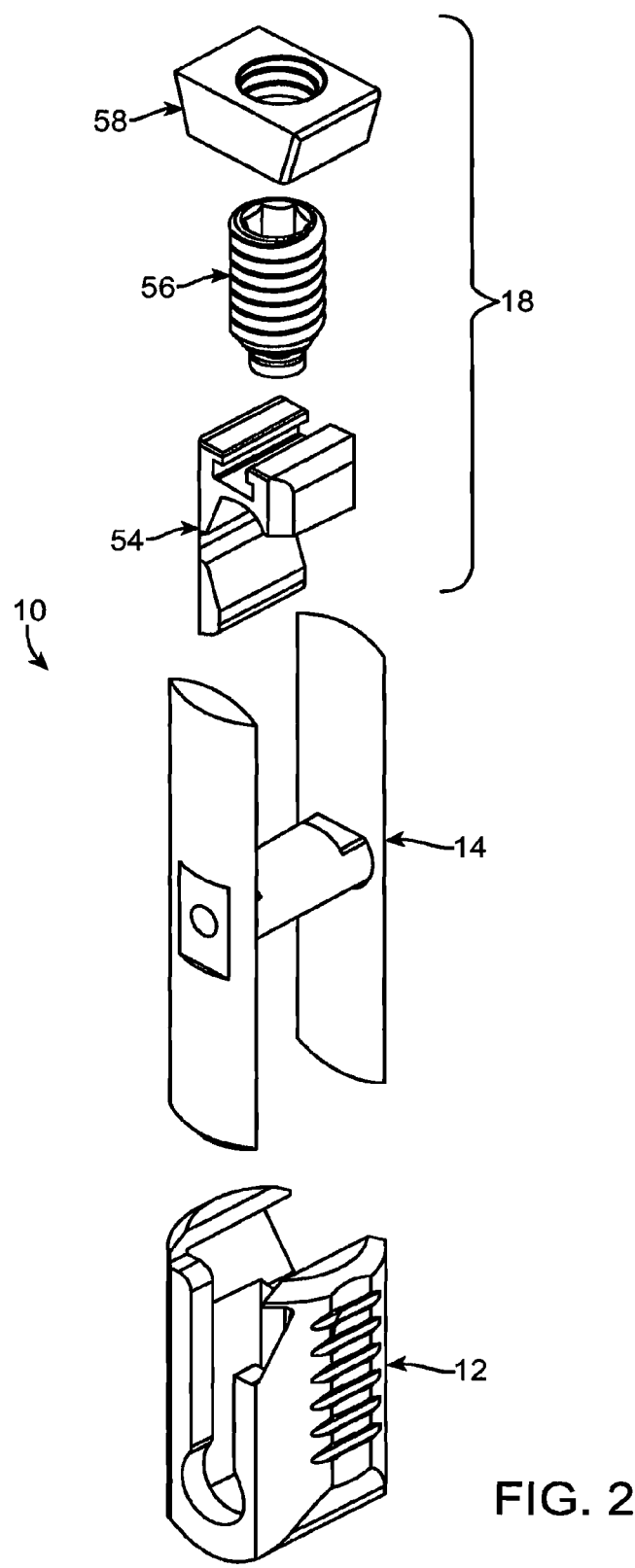
FIG. 2 illustrates an exploded perspective view of a spacer according to the present invention.

Turning to FIG. 2, an exploded perspective view of the spacer 10 is shown illustrating the body 12, wing 14 and components of the actuator assembly 18.

Turning to FIGS. 3a, 3b, 3c and 3d, there is shown a perspective view, side view, top view and sectional view, respectively, of the body 12 according to the present invention. The body 12 has a size and shape that allows for implantation between adjacent spinous processes and facilitates delivery into a patient through a narrow port or cannula. The body 12 has a proximal end 20 and a distal end 22 and two oppositely located sidewalls 24 integrally joined at the distal end 22. When implanted in an interspinous process space, one of the sidewalls 24 serves as a superior spinous process engaging surface and the other serves as an inferior spinous process engaging surface. In one variation, the sidewalls 24 are substantially flat surfaces and substantially parallel to each other. The body 12 forms a generally U-shaped channel between the sidewalls 24 with the open end of the U-shaped channel located at the proximal end 20.

Inside the body 12, the body 12 defines an actuator assembly receiving portion 26 and a wing receiving portion 28 between the sidewalls 24. The wing receiving portion 28 is located near the distal end 22 of the body 12 and is connected to the actuator assembly receiving portion 26 which together form the U-shaped passageway 30 inside the body 12. The wing receiving portion 28 is arcuate in shape which provides the wing 14 with a smooth bearing surface for rotation. The actuator assembly receiving portion 26 includes a body link receiving portion 32.

Figure 3A:
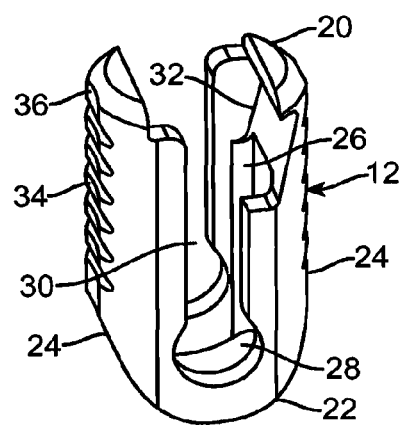
FIG. 3a illustrates a perspective view of a body of a spacer according to the present invention.
Figure 3B:
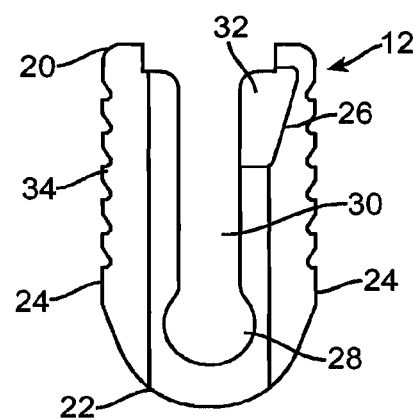
FIG. 3b illustrates a side view of a body of a spacer according to the present invention.
Figure 3C:
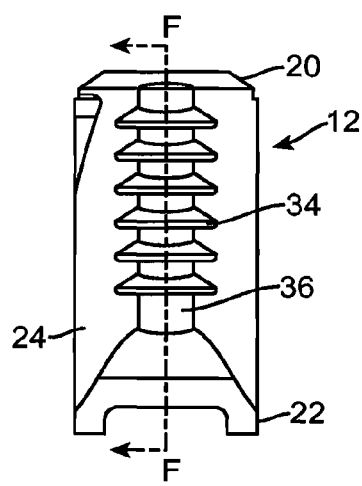
FIG. 3c illustrates a top view of a body of a spacer according to the present invention.
Figure 3D:
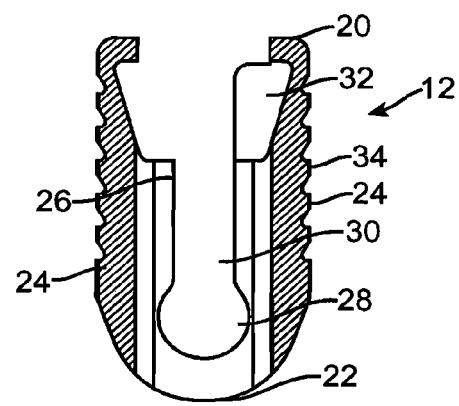
FIG. 3d illustrates a cross-sectional view taken along line F-F in FIG. 3c of a body of a spacer according to the present invention.

The outside of the body 12 includes ridges 34 along at least a portion of the sidewalls 24. In one variation, the body 12 does not include ridges 34. The ridges 34 and sidewalls 24 on which they are formed function to provide a traction surface for contact with the ends of the spinous processes of the superior and inferior vertebrae or other tissue of the interspinous process space between which the spacer 10 is implanted. When implanted, one of the sidewalls 24 faces the superior spinous process and the other sidewall 24 facet the inferior spinous process. The distance between sidewalls is sufficient to occupy the interspinous process space according to surgeon preference. In one variation, the ridges 34 are angled towards the proximal end 20 to ease insertion and help prevent the spacer from backing out as the ridges grip the spinous processes and adjacent tissue to help keep the spacer 10 in place. In one variation, as shown in FIG. 3c, a slight saddle-shaped channel or scallop 36 is formed on the outer surface of the sidewalls 24 extending longitudinally between the proximal end 20 and the distal end 22 to help seat, conform and center the body 12 between spinous processes. The channel 36 is shown in conjunction with ridges 34 in FIGS. 3a and 3c. The distal tip 22 of the spacer body 12 is rounded to ease passage of the spacer 10 through tissue and ligament. The distal tip 22 serves as the leading end of the spacer 10 being positionable closer to the spinal canal relative to the proximal end 20.

Figure 4A:
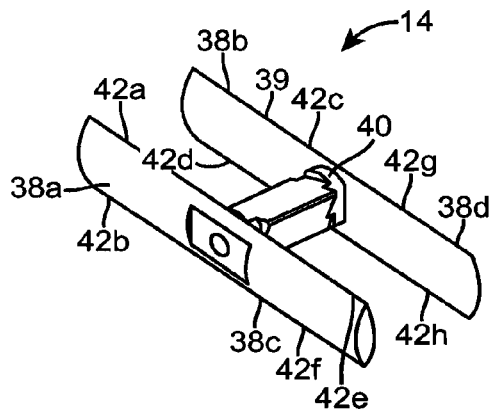
FIG. 4a illustrates a perspective view of a wing according to the present invention.
Figure 4B:
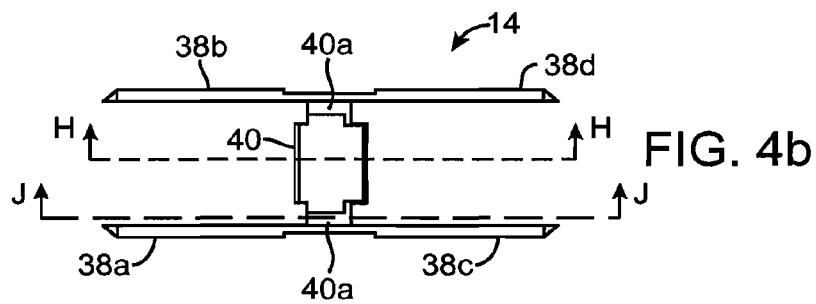
FIG. 4b illustrates a top view of a wing according to the present invention.
Figure 4C:
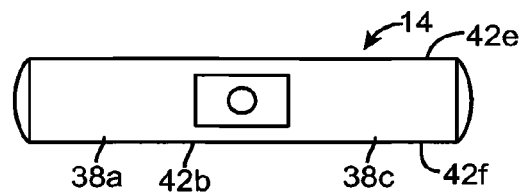
FIG. 4c illustrates a side view of a wing according to the present invention.
Figure 4D:
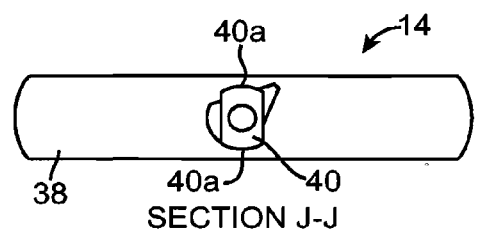
FIG. 4d illustrates a cross-sectional view taken along line J-J in FIG. 4b of a body of a spacer according to the present invention.

With reference now to FIGS. 4a-4e, there is shown a perspective, top, side, a first cross-sectional and a second cross-section view, respectively, of the wing 14 according to the present invention. The wing 14 includes at least two extending members 38a, 38b interconnected by a cross-member 40 that together form a single U-shaped channel. In the variation shown in FIGS. 4a-4e, four extending members 38a, 38b, 38c and 38d are part of the spacer 10. The four extending members 38a, 38b, 38c and 38d are interconnected by at least one cross-member 40 and form two adjacent generally U-shaped channels such that together, the U-shaped channels form a generally H-shaped wing 14 as seen in FIG. 4b. One substantially U-shaped channel is defined between extending members 38a and 38b configured and sized for receiving a superior spinous process and laterally retaining the spacer with respect to the superior spinous process and a second substantially U-shaped channel is defined between extending members 38c and 38d configured and sized for receiving an inferior spinous process and laterally retaining the spacer with respect to the inferior spinous process. The inner surfaces of the extending members may contact or engage or conform to and generally face the lateral sides of the spinous processes when the spacer is implanted. In this regard, the extending members are configured and dimensioned to generally prevent or limit lateral movement of the spacer when the spacer is implanted. In the variation shown, extending members 38a and 38c form one side of the wing 14 and have longitudinal axes that are coincident. Also, extending members 38b and 38d form a second side of the wing 14 and have longitudinal axes that are coincident. Each extending member 38a, 38b, 38c, 38d is substantially rectangular in shape. In another variation, the extending is any suitable shape for preventing or limiting lateral movement of the spacer with respect to at least one of the spinous processes. Each extending member 38a-38d includes a substantially flat inner surface and a slightly curved outer surface. The curved outer surface contributes to the bullet-like profile of the spacer 10 when in the undeployed configuration and conforms more closely to the shape of the body 12 to ease installation as the spacer is moved through tissue to the interspinous process space. The flat inner surface and the curved outer surface of each extending member 38 meet to form edges 42a, 42b, 42c, 42d. In one variation, the edges 42a, 42b, 42c, 42d are relatively sharp and therefore, advantageous for passing or cutting through tissue as the wing 14 is moved from an undeployed configuration to a deployed configuration.

Figure 4E:
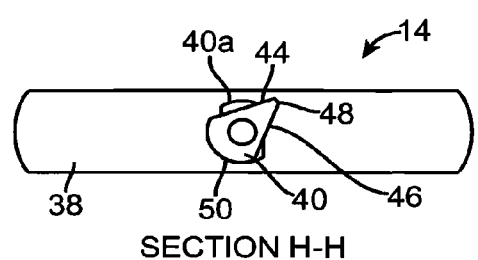
FIG. 4e illustrates a cross-sectional view taken along line H-H in FIG. 4b of a body of a spacer according to the present invention.

With particular reference to FIG. 4e, the cross-member 40 includes a first earning surface 44 and a second earning surface 46. The first and second earning surfaces 44, 46 are angled with respect to each other to form a wedge-shape such that one end forms a pointed lock engaging end 48 for engaging with the actuator and the other end forms a curved seating end 50 for seating in the wing receiving portion 28 of the body 12. The cross-member 40 includes end portions 40a configured as curved seating surfaces for seating in the wing receiving portion 28 of the body 12. The curved seating surfaces extend around at least half of the circumference of the cross-member 40. The cross-member 40 is fixed with respect to the extending members 38a, 38b, 38c, 38d such that movement of the cross-member 40 translates to movement of the extending members 38a, 38b, 38c, 38d.

With brief reference back to FIG. 2, the actuator assembly 18 will now be described. The actuator assembly 18 includes an actuator 54, a shaft 56 and an optional body link 58. The body link 58 and actuator 54 are connected to the shaft 56.

Figure 5A:
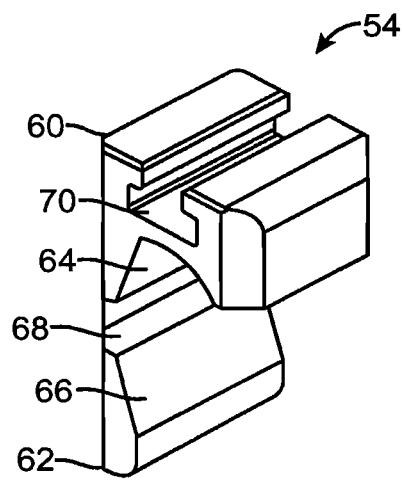
FIG. 5a illustrates a perspective view of an actuator of a spacer according to the present invention.
Figure 5B:
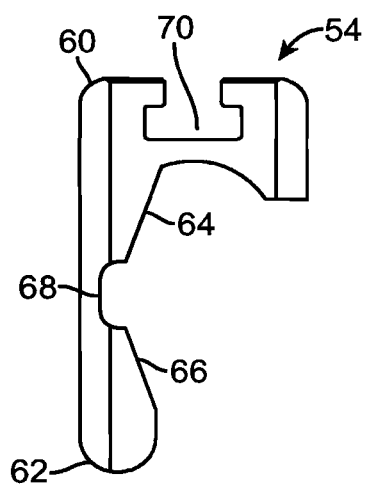
FIG. 5b illustrates a side view of an actuator of a spacer according to the present invention.

Turning now to FIGS. 5a and 5b, the actuator 54 will now be described. The actuator 54 includes a proximal end 60 and a distal end 62, a first surface 64, a second surface 66, a receiving portion 68 for the pointed lock engaging end 48 of the cross member 40 and a shaft receiving portion 70 configured to receive the shaft 56. The first surface 64 is configured to conform and correspond to the first caming surface 44 and curved seating end 50 of the cross member 40 when the spacer 10 is in the undeployed configuration such that the first caming surface 44 and curved seating end 50 of the cross member 40 are in juxtaposition with the first surface 64 of the actuator 54. The second surface 66 is configured to conform and correspond to the second caming surface 46 of the cross member 40 when the spacer is in the deployed configuration. The first surface 64 and the second surface 66 define a wedge-shaped space for receiving the cross-member 40. The receiving portion 68 is configured to receive and retain the pointed lock engaging end 48 of the cross member 40. First and second surfaces 64 and 66 are configured to be substantially at the same angle with respect to the longitudinal axis permitting rotation of the cross-member by approximately 90 degrees. The first and second surfaces 64 and 66 in conjunction with the receiving portion 68 serve as bearing surfaces for the first and second caming surfaces 44, 46 to effect rotation of the wing 14 to and from an undeployed configuration and a deployed configuration. In one variation, the first surface 64 bears at least part of the force from the first earning surface 44 for moving the wing 14 from a first position to a second position and the second surface 66 bears at least part of the force from the second caming surface 46 when the wing is in the second position preventing the wing from over-rotation. The distal end 62 of the actuator 54 is bulbous and configured to retain the cross member 40 within the actuator 54 when the spacer 10 is assembled.

Figure 6A:
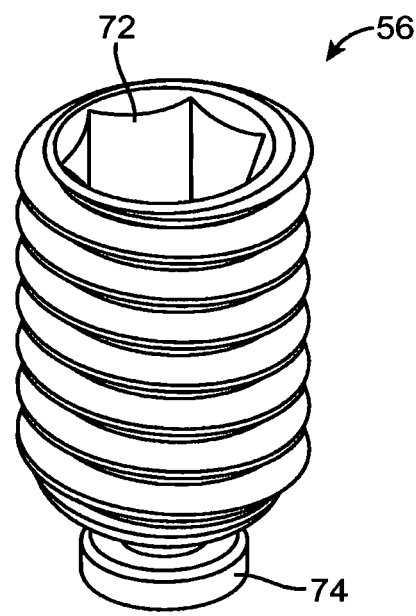
FIG. 6a illustrates a perspective view of a shaft of a spacer according to the present invention.
Figure 6B:
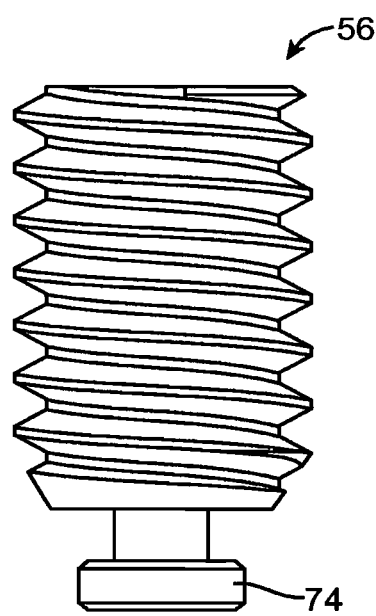
FIG. 6b illustrates a side view of a shaft of a spacer according to the present invention.

Turning now to FIGS. 6a and 6b, the shaft 56 of the actuator assembly 18 will now be described. The shaft 56 is substantially cylindrical in shape and, in one variation, includes a threaded outer surface for engagement with the threaded inner surface of the body link 58. In a variation without a body link 58, the threaded outer surface of the shaft 56 engages with a threaded inner surface of the body 12. The proximal end of the shaft 56 includes a socket 72 such as a hex socket for receiving a hexagonally-shaped driving tool. When the spacer 10 is assembled, the proximal end of the shaft 56 is accessible at the proximal end of the spacer 10 for connection with a driving tool. The distal end of the shaft 56 includes an actuator engagement portion 74 configured to connect to the actuator 54. The actuator engagement portion 74 is a projection that connects to the shaft receiving portion 70 on the actuator 54.

Figure 7A:
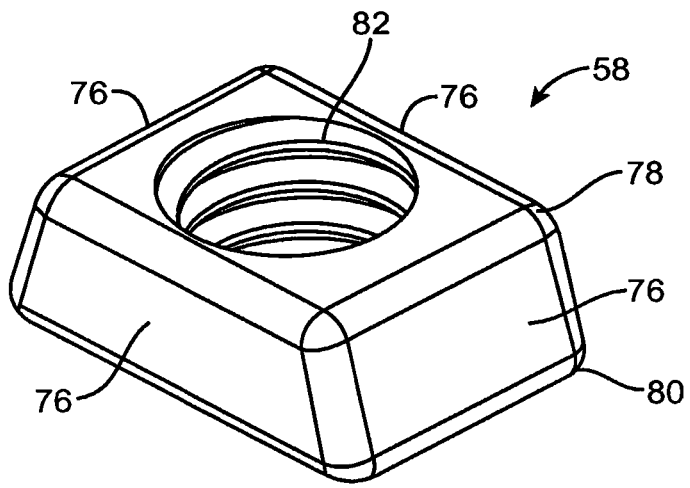
FIG. 7a illustrates a perspective view of a body link of a spacer according to the present invention.
Figure 7B:
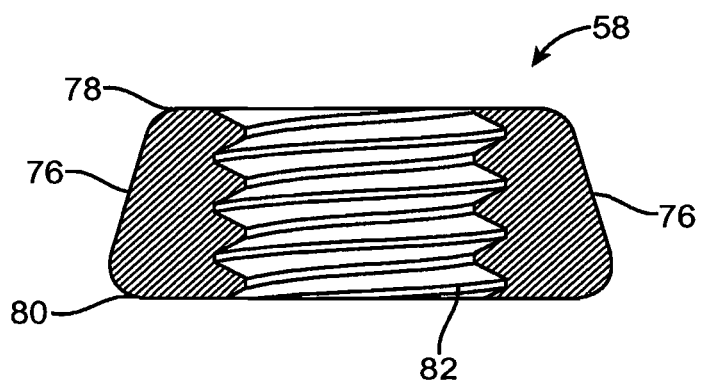
FIG. 7b illustrates a cross-sectional view of a body link of a spacer according to the present invention.

Turning now to FIGS. 7a and 7b, the body link 58 will now be described. The body link 58 is sized and configured to be disposed inside the link receiving portion 32 of the body 12 and configured to link the shaft 56 to the body 12. The body link 58 includes a threaded bore 82 configured to receive the threaded shaft 56. In the variation of FIGS. 7a and 7b, the body link 58 further functions as a body expander such that the body link 58 includes at least one diverging outer surface 76. The at least one angled surface is configured such that it diverges from proximal end 78 toward the distal end 80 of the body link 58. As a result, the body link 58 is larger at the distal end 80 relative to the proximal end 78. In the variation shown in FIGS. 7a and 7b, the angled outer surface 76 comprises four angled sides which in combination diverge outwardly from the proximal end 78 toward the distal end 80 to form a wedge-like shape. However, the invention is not so limited so long as the body link 58 has a diverging surface. Another example of a diverging body link 58 is a body link 58 having a cone-shaped outer surface. Whether the variation of the spacer includes a diverging or non-diverging body link 50, the shape of the link receiving portion 32 corresponds to the shape of the body link 50 and the link receiving portion 32 is sufficiently large enough to permit the body link 50 to travel inside it as the shaft 56 is moved to deploy the wing 14.

Assembly of the actuator assembly 18 will now be described in reference to FIGS. 2, 5a, 5b, 6a, 6b, 7a and 7b. The shaft 56 of the actuator assembly 18 is connected to the actuator 54 by inserting the actuator engagement portion 74 of the shaft 56 into the shaft receiving portion 70 of actuator 54. The shaft receiving portion 70 is a slot with a constricted neck portion into which the actuator engagement portion 74 of the shaft 56 slides laterally into and cannot be removed along the longitudinal axis. The shaft 56 is connected to the body link 58 by inserting the threaded portion of the shaft 56 into the threaded bore 82 of the body link 58 to complete the assembly of the actuator assembly 18.

Assembly of the remainder of the spacer 10 will now be described. The wing 14 is connected to the actuator assembly 18. The wing 14 is connected to the actuator 54 such that the pointed lock engaging end 48 of the cross member 40 of the wing 14 is inserted into the receiving portion 68 of the actuator 54. The wing 14 and actuator assembly 18 are inserted through the opening at the proximal end 20 of the body 12 until the wing 14 is seated in the wing receiving portion 28, the actuator assembly 18 is disposed inside the actuator assembly receiving portion 26 and the body link 58 is located in the body link receiving portion 32. The end portions 40a of the cross-member 40 rest against corresponding curved surfaces of the wing receiving portion 28 of the body 12 advantageously providing a large contact surface area suitable for bearing large loads, in particular, shear forces on the wing. The body link 58 is inserted and snapped through the opening at the proximal end 20 of the body 12 into the complementarily-shaped body link receiving portion 32 and retained therein via an interference fit engagement with the body 12. With the body link 58 in place, the wing 14 and the actuator assembly 18 are secured inside the body 12. The wing 14 is seated in wing receiving portion 28 such that wing 14 is capable of rotational movement with respect to the body 12.

Once assembled, the spacer 10 is ready for delivery into the patient. To deliver the spacer 10 within the patient, the spacer 10 is releasably attached to a delivery instrument (not shown). For example, a delivery instrument may connect to the proximal end 20 of the spacer 10 via notches (not shown) formed in the body 12 or connect to outer holes (not shown) formed in the cross member 40 of the wing 14. The spacer 10 is provided or otherwise placed in its undeployed state or closed configuration as illustrated in FIG. 1a wherein at least a part of the length of the wing 14 shares/overlaps a part of the length of the body 12 when in an undeployed configuration and, in particular, at least half of the length of the wing 14 is shared/overlapped by the length of the body 12. A small midline or lateral-to-midline posterior incision is made in the patient for minimally-invasive percutaneous delivery. In one variation, the supraspinous ligament is avoided. In another variation, the supraspinous ligament is split longitudinally along the direction of the tissue fibers to create an opening for the instrument. Dilators may be further employed to create the opening. In the undeployed state and attached to a delivery instrument, the spacer 10 is inserted through a port or cannula, if one is employed, which has been operatively positioned to an interspinous process space within a patient's back with the proximal end extending outside the patient. In some circumstances, it may not be necessary to use a cannula where the device is inserted with the delivery instrument alone or through a larger opening in the tissue. The spacer is then advanced to within the targeted interspinous process space between two adjacent spinous processes. If a cannula is employed, the spacer 10 is advanced beyond the end of the cannula or, alternatively, the cannula is pulled proximately to uncover the spacer 10 within. The surgeon may examine the positioning of the spacer 10 via fluoroscopy and reposition it if necessary.

Figure 8:
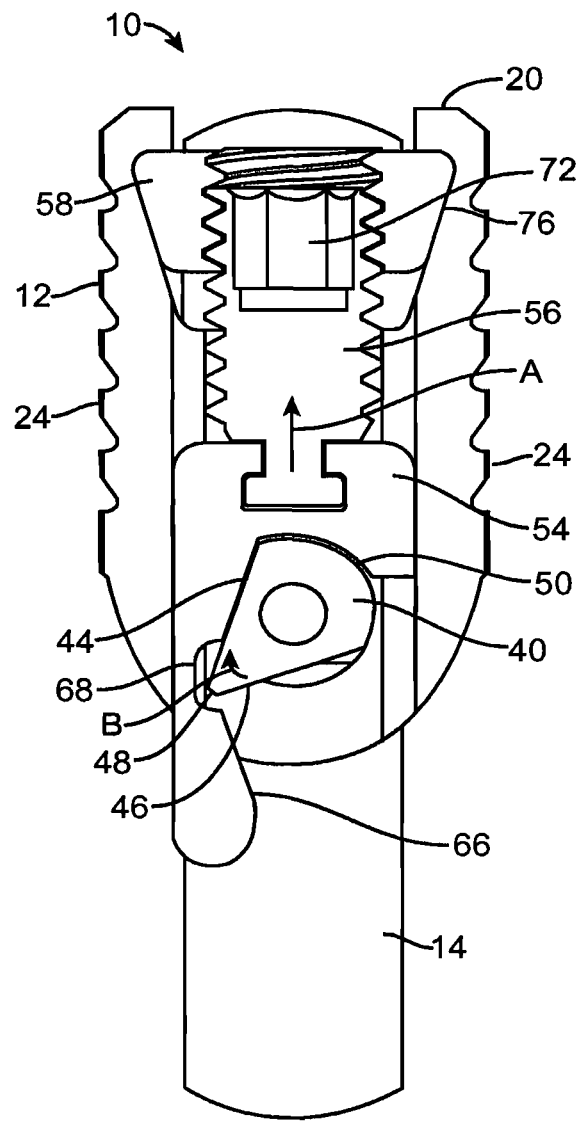
FIG. 8 illustrates a cross-sectional view of a spacer in an undeployed configuration according to the present invention.
Figure 9:
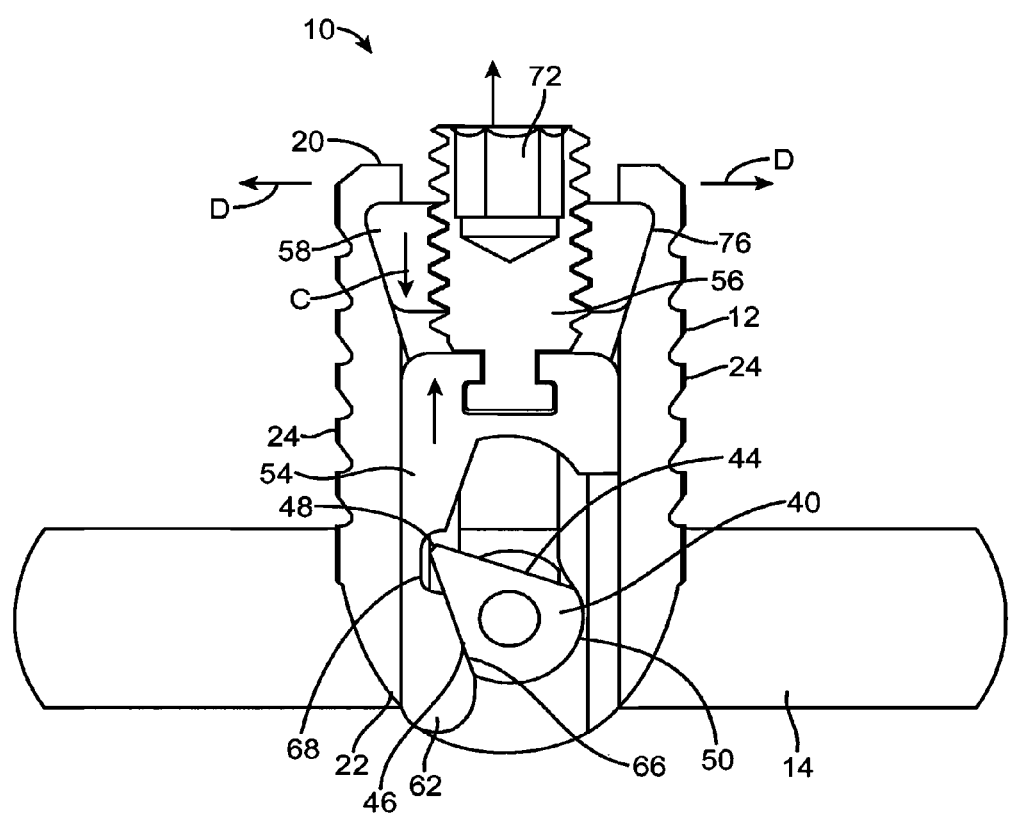
FIG. 9 illustrates a cross-sectional view of a spacer in a deployed configuration according to the present invention.

With particular reference now to FIGS. 8 and 9, deployment of the spacer 10 from an undeployed configuration illustrated in FIG. 8 to a deployed configuration illustrated in FIG. 9 while positioned within the interspinous process space will now be described. With particular reference first to FIG. 8, a driver (not shown) such as a hex-shaped tool is inserted into the hex socket 72 of the shaft 56 and turned to move or pull the shaft 56 towards the proximal end 20 of the body 12 in a direction indicated by the arrow "A". Since the actuator 54 is connected to the shaft 56, the actuator 54 also moves (is pulled) towards the proximal end 20 rotating the wing 14 in a direction indicated by the arrow "B". The entire wing 14 rotates through an angle of approximately 90 degrees from the undeployed configuration through intermediate configurations into the second or deployed configuration shown in FIG. 9 in which the wing 14 is perpendicular to the longitudinal length of the body 12. The proximal direction of motion of the shaft 56 and connected actuator 54 relative to the body 12 (pull deployment) advantageously avoids pushing the spacer 10 deeper into the interspinous space and towards the spinal canal during the process of deployment. Instead, the proximal direction of motion or pulling of the actuator assembly 18 provides for a safer implant and a secure positioning casing installation for the surgeon. The surgeon may examine the positioning of the spacer 10 via fluoroscopy with the spacer 10 in an intermediate configuration and choose to reposition it by moving the spacer 10 along a general posterior-anterior direction with the wings 14 partially deployed. Alternatively, the surgeon may choose to reposition the spacer 10 by returning the spacer 10 to first or closed configuration by rotating the driver in an opposite direction and then moving the spacer 10 into position and continuing with deployment of the wings 14.

With particular reference to FIG. 9, in the deployed configuration the second surface 66 of the actuator 54 abuts the second earning surface 46 of the cross member 40. Further rotation of the wing 14 is prevented by the bulbous distal end 62 being lodged or wedged between the cross member 40 and distal end 22 of the body 12. If the shaft 56 is further proximally advanced pulling the actuator 54 proximally along with it, the wing 14 will not rotate any further; however, in a variation of the spacer 10 that includes a body link 58 that functions as an expander as described above, the body link 58 will advance distally in a direction indicated by arrow "C" in FIG. 9. The diverging outer surface 76 of the body link 58 will wedge toward the distal end 22 spreading the proximal end 20 of the sidewalls 24 outwardly in a direction indicated by arrows "D" relative to the distal end of the sidewalls 24. The spring force of the outwardly biased sidewalls 24 will exert a force from both directions back onto the shaft 56 tightening it in place, thereby, advantageously providing a self locking feature that prevents the threaded shaft or screw 56 from backing out and the caming collapsing. Also, the expanded proximal end 20 of the sidewalls 24 provides additional customized distraction of the spinous processes. The surgeon can drive the shaft 56 to further spread the sidewalls 24 thereby providing greater distraction of the spinous processes according to surgeon preference giving the surgeon additional flexibility in selecting the degree of distraction for a particular patient. Furthermore, the outwardly expanded proximal end 20 of the sidewalls 24 creates a wedge-shaped seat for the spinous process. With the sidewalls 24 in an expanded configuration, the spacer 10 assumes an overall wedge-like shape advantageous for retainment in the interspinous process space. With the sidewalls 24 in an expanded configuration the wedge-shaped seat forms an angle between the sidewall 24 and the wing 14 that is slightly less than 90 degrees on each side of the body 12. This feature advantageously secures the spacer 10 within the patient and helps keep it in place between spinous processes.

Figure 10:
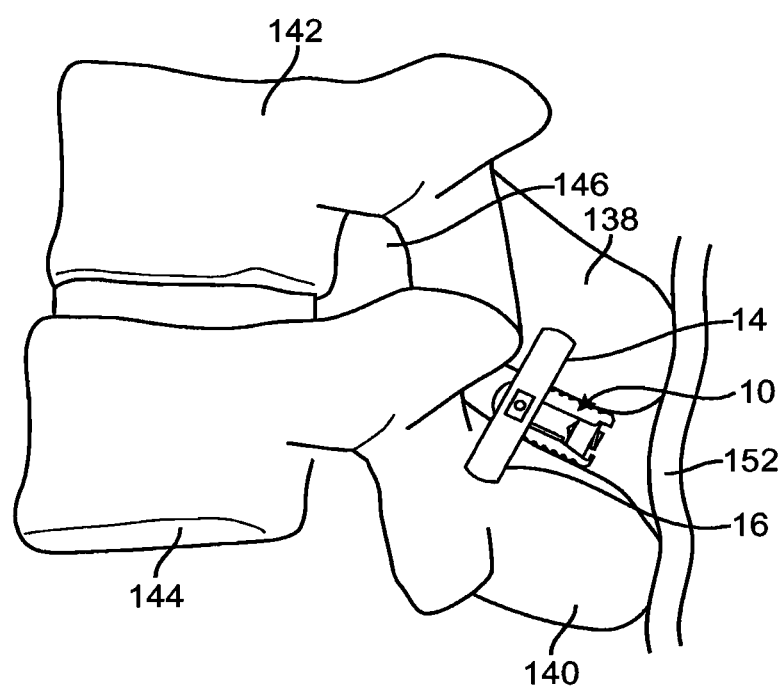
FIG. 10 illustrates a spacer according to the present invention deployed in an Interspinous process space between two adjacent vertebral bodies and a supraspinous ligament.

The spacer 10 may be undeployed for removal from the interspinous space by rotating the shaft 56 in the opposite direction to fold the wing 14 into the closed or undeployed configuration or any intermediate configuration. In the undeployed configuration, the spacer 10 can be removed from the patient or re-adjusted and re-positioned and then re-deployed as needed. This process can be repeated as necessary until the clinician has achieved the desired positioning of the spacer in the patient. Following final positioning, the driver and delivery instrument is detached from the spacer 10 and removed from the operative site leaving the spacer 10 implanted in the interspinous process space as shown in FIG. 10. In FIG. 10, the spacer 10 is shown with the wing 14 receiving the superior spinous process 138 of a first vertebral body 142 and the inferior spinous process 140 of an adjacent second vertebral body 144 providing sufficient distraction/spacing to open the neural foramen 146 to relieve pain. In one variation of the spacer 10 of the present invention, the spacer 10 is configured such that the body 12 seats the superior and inferior spinous processes 138, 140 at a location along the length of the body 12 that is outside location of the wing 14 when in the deployed configuration. Hence, the wing 14 serves as a lateral stabilizer, locator for the spacer 10 instead of a seating location for the spinous processes 138, 140. Therefore, the spacer 10 provides for a longer seating location for the superior and inferior spinous processes making it easier for the surgeon to install the spacer 10. In one variation, the shape of the arm 14 is such that it conforms to the spinous processes 138, 140. The supraspinous ligament 152 is also shown in FIG. 10. The spacer 10 maintains the spinous processes in a distracted or spaced condition, for example where the distance of the implant is greater than a pre-implantation distance between the spinous processes.

The wing 14 is movably or rotatably connected to the body 12 to provide rotational movement from an undeployed configuration to a deployed configuration that arcs through about a 90 degree range or more. The wing 14 is rotationally movable between at least an undeployed, collapsed or folded state (as shown in FIG. 8) and a fully deployed state (as shown in FIG. 9). In the undeployed state, the wing 14 is aligned generally or substantially axially (i.e., axially with the longitudinal axis defined by the body 12 or to the translation path into the interspinous process space of the patient) to provide a minimal lateral or radial profile. In the deployed state, the wing 14 is positioned generally or substantially transverse to the collapsed position (i.e., transverse to the longitudinal axis defined by the body 12 or to the translation path into the interspinous space of the patient). In another variation, the wing 14 may also be linearly moveable or translatable from the deployed state to and from an additionally extended state. More specifically, the wing 14 can be extended in the general vertical or horizontal direction along an axis substantially parallel or perpendicular to the spine. The wing 14 is connected to the body 12 in a manner that enables it to be moved simultaneously or independently of each other, as well as in a manner that provides passive deployment and/or vertical extension or, alternatively, active or actuated deployment and/or vertical extension.

The spacer 10 is as easily and quickly removed from the body of the patient as it is installed. To remove the spacer 10, the delivery instrument is inserted into an incision and reconnected to the spacer 10. The shaft 56 is rotated in the opposite direction via a driver to fold the wing 14 into a closed or undeployed configuration such that the wing 10 is clear or disengaged from the superior and inferior spinous processes. In the undeployed configuration, the spacer 10 can be removed from the patient along with the instrument or, of course, re-adjusted and re-positioned and then re-deployed as needed with the benefit of minimal invasiveness to the patient.

Any of the spacers disclosed herein are configured for implantation employing minimally invasive techniques including through a small percutaneous incision and through the superspinous ligament. Implantation through the superspinous ligament involves selective dissection of the superspinous ligament in which the fibers of the ligament are separated or spread apart from each other in a manner to maintain as much of the ligament intact as possible. This approach avoids crosswise dissection or cutting of the ligament and thereby reduces the healing time and minimizes the amount of instability to the affected spinal segment. While this approach is ideally suited to be performed through a posterior or midline incision, the approach may also be performed through one or more incisions made laterally of the spine with or without affect to the superspinous ligament. Of course, the spacer may also be implanted in a lateral approach that circumvents the superspinous ligament altogether.

Other variations and features of the various mechanical spacers are covered by the present invention. For example, a spacer may include only a single U-shaped arm which is configured to receive either the superior spinous process or the inferior spinous process. The surface of the spacer body opposite the side of the single arm may be contoured or otherwise configured to engage the opposing spinous process wherein the spacer is sized to be securely positioned in the interspinous space and provide the desired distraction of the spinous processes defining such space.

Furthermore, depending on the variation of the spacer employed, distraction of the interspinous space is provided by the body of the spacer such that the superior and inferior spinous processes rest on either side of the body and the H-shaped wing keeps the spacer in position with each U of the H-shaped wing encompassing at least a portion of the spinous process. Alternatively, distraction of the interspinous process space is provided by the wing such that each U of the H-shaped wing supports the superior and inferior spinous processes within the U-shaped saddle. The U-shaped saddle can be made shallower or deeper to provide a desired amount of distraction for the spinous processes.

The extension arms of the subject device may be configured to be selectively movable subsequent to implantation, either to a fixed position prior to closure of the access site or otherwise enabled or allowed to move in response to normal spinal motion exerted on the device after deployment. The deployment angles of the extension arms may range from less than 90 degrees (relative to the longitudinal axis defined by the device body) or may extend beyond 90 degrees. Each extension member may be rotationally movable within a range that is different from that of the other extension members. Additionally, the individual superior and/or inferior extensions may be movable in any direction relative to the strut or bridge extending between an arm pair or relative to the device body in order to provide shock absorption and/or function as a motion limiter, or serve as a lateral adjustment particularly during lateral bending and axial rotation of the spine. The manner of attachment or affixation of the extensions to the arms may be selected so as to provide movement of the extensions that is passive or active or both. In one variation, the saddle or distance between extensions can be made wider to assist in seating the spinous process and then narrowed to secure the spinous process positioned between extensions.

The disclosed devices or any of their components can be made of any biologically adaptable or compatible materials. Materials considered acceptable for biological implantation are well known and include, but are not limited to, stainless steel, titanium, tantalum, combination metallic alloys, various plastics, polymers, resins, ceramics, biologically absorbable materials and the like. Polymers including PEEK, PEK, PAEK, PEKEKK or any polyetherketone or polyetherketone metal composite can be employed. In the variation in which the body link 58 is configured as an expander, a slightly flexible construction of the body 12 is desirable to effect the desired self-locking features described above in which case suitable materials such as polymeric materials are appropriately selected for the entire spacer or for selected components of the spacer. Any component may be also coated/made with osteo-conductive (such as demineriized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, a surface of any of the implants may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone ingrowth or establish a mineralized connection between the bone and the implant, and reduce the likelihood of implant loosening. Lastly, any assembly or its components can also be entirely or partially made of a shape memory material or other deformable material.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. A method for treating a subject, comprising:
splitting the subject's supraspinous ligament to create an opening;
moving a cannula through the opening located generally along the subject's midline;
delivering an interspinous implant device through the cannula and to an interspinous space along the subject's spine;
rotating a first rotating member of the interspinous implant device to move a first superior extension of the first rotating member along a first side of a superior spinous process and to move a first inferior extension of the first rotating member along a first side of an inferior spinous process;
rotating a second rotating member of the interspinous implant device to move a second superior extension of the second rotating member along a second side of the superior spinous process and to move a second inferior extension of the second rotating member along a second side of the inferior spinous process; and
removing the cannula from the subject while the superior spinous process is positioned directly between the first and second superior extensions and the inferior spinous process is positioned directly between the first and second inferior extensions.

2. The method of claim 1, further comprising:
concurrently rotating the first and second rotating members by using the delivering instrument connected to the interspinous implant device and extending through the cannula;
separating the delivery instrument from the interspinous implant device; and
removing the delivery instrument from the cannula.

3. The method of claim 1, wherein delivering the interspinous implant device through the cannula includes moving the interspinous implant device along the passageway of the cannula while longitudinal axes of the first and second rotating members are aligned with the passageway.

4. The method of claim 1, wherein rotating the first and second rotating members includes:
rotating the first and second superior extensions together in a superior direction relative to the subject's spine so as to position the superior spinous process directly between the first and second superior extensions; and
rotating the first and second inferior extensions together in an inferior direction relative to the subject's spine so as to position the inferior spinous process directly between the first and second inferior extensions.

5. The method of claim 1, further comprising rotating the first and second rotating members about a common rotational axis.

6. The method of claim 1, wherein rotating the first and second rotating members includes rotating each of the first and second rotating members relative to a main body of the interspinous spacer about 90 degrees.

7. The method of claim 1, wherein rotating the first rotating member includes rotating the first rotating member relative to a main body of the interspinous spacer less than about 90 degrees.

8. The method of claim 1, wherein rotating the first rotating member includes rotating the first rotating member relative to a main body of the interspinous spacer more than about 90 degrees.

9. A method for treating a subject, comprising:
moving a cannula through an opening located generally along the subject's midline;
delivering an interspinous implant device through the cannula and to an interspinous space along the subject's spine;
rotating a first rotating member of the interspinous implant device to move a first superior extension of the first rotating member along a first side of a superior spinous process and to move a first inferior extension of the first rotating member along a first side of an inferior spinous process;
rotating a second rotating member of the interspinous implant device to move a second superior extension of the second rotating member along a second side of the superior spinous process and to move a second inferior extension of the second rotating member along a second side of the inferior spinous process; and
removing the cannula from the subject while the superior spinous process is positioned directly between the first and second superior extensions and the inferior spinous process is positioned directly between the first and second inferior extensions,
wherein the method further comprises:
moving an end of the cannula through a supraspinous ligament of the subject;
advancing the interspinous implant device along a passageway of the cannula while longitudinal axes of the first and second rotating members extend in a direction substantially parallel to a longitudinal axis of the passageway; and after delivering the interspinous implant device through the cannula, driving an actuator of the interspinous implant device using a delivery instrument connected to the interspinous implant device to cause rotation of the first and second rotating members.

10. A method for treating a subject, comprising:

positioning a cannula through the subject's supraspinous ligament;

delivering an interspinous spacer through the cannula and to an interspinous space in the subject; and rotating a wing assembly of the interspinous spacer relative to a body of the interspinous spacer while the body is located at the interspinous space such that
first and second superior extensions of the wing assembly move superiorly relative to the subject's spine to position the subject's superior spinous process between the first and second superior extensions, and
first and second inferior extensions of the wing assembly move inferiorly relative to the subject's spine to position the subject's inferior spinous process between the first and second inferior extensions.

11. The method of claim 10, further comprising rotating first and second elongate members of the wing assembly together about an axis of rotation extending through the body of the interspinous spacer positioned between the first and second elongate members to move the wing assembly from a delivery configuration for delivery into the interspinous space to a deployed configuration for spacing apart the superior and inferior spinous processes.

12. The method of claim 10, further comprising:

advancing the interspinous spacer along a passageway of the cannula while the first and second superior extensions and the first and second inferior extensions extend in a direction substantially parallel to a longitudinal axis of the passageway; and after delivering the interspinous spacer through the cannula, operating a delivery instrument extending through the cannula and connected to the interspinous spacer to drive an actuator of the interspinous spacer which causes rotation of the wing assembly.

13. The method of claim 10, further comprising:

mechanically driving an actuator of the interspinous spacer using a delivery instrument to gradually rotate the wing assembly; and separating the delivery instrument from the interspinous spacer which is positioned at the interspinous space.

14. The method of claim 10, wherein the first superior extension and the first inferior extension are part of a first rotatable member, wherein the second superior extension and the second inferior extension are part of a second rotatable member, and the method further includes:

pivoting the first and second rotatable members relative to the body about a common axis of rotation that is generally perpendicular a sagittal plane of the interspinous spacer to rotate the wing assembly.

15. The method of claim 14, wherein most of the body is positioned directly between the first and second rotatable members while the interspinous spacer is delivered through the cannula.

16. The method of claim 14, wherein the first and second rotatable members are substantially parallel to one another while the interspinous spacer is delivered through the cannula.

17. A minimally-invasive percutaneous method for treating a subject, comprising:

moving an interspinous spacer in a delivery configuration along an anterior-to-posterior delivery path and to an interspinous space, wherein the interspinous spacer includes—
a body with an actuator,
a first elongate member, and
a second elongate member, wherein the first and second elongate members are pivotally coupled to and aligned with the body when the interspinous spacer is in the delivery configuration; and driving the actuator using a delivery instrument releasably connected to the interspinous spacer to pivot the first and second elongate members relative to the body so as to move the interspinous spacer to a deployed configuration such that a superior spinous process is located directly between the first and second elongate members and an inferior spinous process is located directly between the first and second elongate members, wherein the method further comprises
moving an end of the cannula through a supraspinous ligament of the subject; and
moving the interspinous spacer along a passageway of the cannula while longitudinal axes of the first and second elongate members extend in a direction substantially parallel to a path of travel of the interspinous spacer along the passageway.

18. The method of claim 17, wherein the entire interspinous spacer is capable of being located inferior relative to the superior spinous process and superior relative to the inferior spinous process when the body of the interspinous spacer, in the delivery configuration, is positioned at the interspinous space.

19. The method of claim 17, further comprising distracting the superior and inferior spinous processes by moving the interspinous spacer to the deployed configuration.

20. The method of claim 17, further comprising moving the interspinous spacer in the delivery configuration through the cannula while the cannula is positioned through the supraspinous ligament.

21. The method of claim 17, further comprising moving at least a portion of the interspinous spacer out of the cannula before pivoting the first and second elongate members relative to the body.

22. A minimally-invasive percutaneous method for treating a subject, comprising:

moving an interspinous spacer in a delivery configuration along an anterior-to-posterior delivery path and to an interspinous space, wherein the interspinous spacer includes—
a body with an actuator,
a first elongate member, and
a second elongate member, wherein the first and second elongate members are pivotally coupled to and aligned with the body when the interspinous spacer is in the delivery configuration; and driving the actuator using a delivery instrument releasably connected to the interspinous spacer to pivot the first and second elongate members relative to the body so as to move the interspinous spacer to a deployed configuration such that a superior spinous process is located directly between the first and second elongate members and an inferior spinous process is located directly between the first and second elongate members wherein the method further comprises operating the delivery instrument to rotate the first and second elongate members together about a common axis of rotation that extends substantially perpendicular to a sagittal plane of the interspinous spacer.

\* \* \* \* \*

UNITED STATES PATENT AND TRADEMARK OFFICE
CERTIFICATE OF CORRECTION

PATENT NO. : 9,861,398 B2
APPLICATION NO. : 14/835195
DATED : January 9, 2018
INVENTOR(S) : Altarac et al.

It is certified that error appears in the above-identified patent and that said Letters Patent is hereby corrected as shown below:

In the Specification

In Column 2, Line 51, delete "earning" and insert -- caming --, therefor.

In Column 2, Line 58, delete "earning" and insert -- caming --, therefor.

In Column 4, Line 10, delete "mad" and insert -- read --, therefor.

In Column 4, Line 60, delete "Interspinous" and insert -- interspinous --, therefor.

In Column 6, Line 19, delete "facet" and insert -- faces --, therefor.

In Column 7, Line 18, after "first" delete "earning" and insert -- caming --, therefor.

In Column 7, Line 18, after "second" delete "earning" and insert -- caming --, therefor.

In Column 7, Line 19, delete "earning" and insert -- caming --, therefor.

In Column 7, Line 63, delete "earning" and insert -- caming --, therefor.

In Column 10, Line 5, delete "casing" and insert -- easing --, therefor.

In Column 10, Line 18, delete "earning" and insert -- caming --, therefor.

In Column 10, Line 36, delete "caming" and insert -- wing --, therefor.

In Column 11, Line 62, delete "superspinous" and insert -- supraspinous --, therefor.

In Column 11, Lines 62-63, delete "superspinous" and insert -- supraspinous --, therefor.

Signed and Sealed this
Nineteenth Day of June, 2018

Andrei Iancu
*Director of the United States Patent and Trademark Office*

In Column 11, Lines 63-64, delete "superspinous" and insert -- supraspinous --, therefor.

In Column 12, Lines 6-7, delete "superspinous" and insert -- supraspinous --, therefor.

In Column 12, Lines 8-9, delete "superspinous" and insert -- supraspinous --, therefor.

In Column 13, Line 3, delete "deminerized" and insert -- demineralized --, therefor.